(12) United States Patent
Wang et al.

(10) Patent No.: US 7,384,922 B2
(45) Date of Patent: Jun. 10, 2008

(54) 6-11 BRIDGED OXIME ERYTHROMYCIN DERIVATIVES

(75) Inventors: Guoqiang Wang, Belmont, MA (US); Ly Tam Phan, Quincy, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 11/416,609

(22) Filed: May 3, 2006

(65) Prior Publication Data

US 2006/0252712 A1 Nov. 9, 2006

Related U.S. Application Data

(60) Provisional application No. 60/677,675, filed on May 4, 2005.

(51) Int. Cl.
*A61K 31/70* (2006.01)
*C07H 17/08* (2006.01)

(52) U.S. Cl. .......................................... 514/29; 536/7.4
(58) Field of Classification Search .................. 536/7.4
See application file for complete search history.

(56) References Cited

U.S. PATENT DOCUMENTS

| 6,046,171 | A | 4/2000 | Or et al. |
|---|---|---|---|
| 6,878,691 | B2 | 4/2005 | Or et al. |
| 2004/0053861 | A1 | 3/2004 | Or et al. |
| 2004/0157787 | A1 | 8/2004 | Or et al. |
| 2005/0009761 | A1 | 1/2005 | Or et al. |
| 2005/0159370 | A1 | 7/2005 | Or et al. |
| 2005/0171033 | A1 | 8/2005 | Qiu et al. |

FOREIGN PATENT DOCUMENTS

| WO | WO 99/21864 | 5/1999 |
|---|---|---|
| WO | WO 03/095466 A1 | 11/2003 |
| WO | WO03/097659 A1 | 11/2003 |

OTHER PUBLICATIONS

8th International Antibacterial Drug Discovery and Development Summit, *Strategic Research Institute*, Mar. 24-25, 2003, Princeton, NJ.
Silverman, R., The Organic Chemistry of Drug Design and Drug Action, (1992) published by Academic Press, pp. 19-21 and 352-397.

*Primary Examiner*—Elli Peselev
(74) *Attorney, Agent, or Firm*—Carolyn S. Elmore; Elmore Patent Law Group

(57) ABSTRACT

The present invention discloses compounds of formula I, or pharmaceutically acceptable salts, esters, or prodrugs thereof:

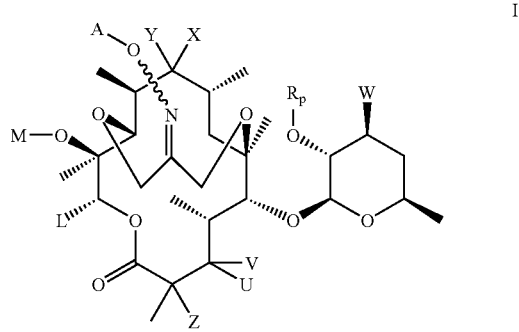

which exhibit antibacterial properties. The present invention further relates to pharmaceutical compositions comprising the aforementioned compounds for administration to a subject in need of antibiotic treatment. The invention also relates to methods of treating a bacterial infection in a subject by administering a pharmaceutical composition comprising the compounds of the present invention. The invention further includes processes by which to make the compounds of the present invention.

11 Claims, No Drawings

6-11 BRIDGED OXIME ERYTHROMYCIN DERIVATIVES

RELATED APPLICATIONS

This application claims the benefit of U.S. application Ser. No. 11/122,251, filed on May 4, 2005 and U.S. Provisional Application No. 60/677,675, filed on May 4, 2005. The entire teachings of the above applications are incorporated herein by reference.

TECHNICAL FIELD

The present invention relates to novel semisynthetic macrolides having antibacterial activity and useful in the treatment and prevention of bacterial infections. More particularly, the invention relates to 6-11 bicyclic macrolide, ketolide, and anhydrolide derivatives, compositions containing such compounds and methods for using the same, as well as processes for making such compounds.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Macrolides are classified according to the size of the lactone ring (12, 14, 15 or 16 atoms). The macrolide antibiotic family (14-, 15- and 16-membered ring derivatives) shows a wide range of characteristics (antibacterial spectrum, side-effects and bioavailability). Among the commonly used macrolides are erythromycin, clarithromycin, and azithromycin. Macrolides possessing a 3-oxo moiety in place of the 3-cladinose sugar are known as ketolides and have shown enhanced activity towards gram-negative bacteria and macrolide resistant gram-positive bacteria. Macrolides possessing a degree of unsaturation between carbons 2 and 3 or between carbons 3 and 4 of the erythromycin macrocycle are known as anhydrolides. The search for macrolide compounds which are active against $MLS_B$-resistant strains ($MLS_B$=Macrolides-Lincosamides-type B Streptogramines) has become a major goal, together with retaining the overall profile of the macrolides in terms of stability, tolerance and pharmacokinetics.

International Application WO 97/42205 of Elliott et al, published Nov. 13, 1997, discloses 3-descladinose-2,3-anhydroerythromycin derivatives having a cyclic carbamate and cyclic carbazate basic nuclear structure. Further details were also disclosed in J. Med. Chem., 41, pp 1651-1659 (1998) and J. Med. Chem., 41, pp 1660-1670 (1998) by Elliott et al, and by Griesgraber et al, respectively.

U.S. Pat. No. 5,444,051 discloses certain 6-O-substituted-3-oxoerythromycin A derivatives. PCT application WO 97/10251, published Mar. 20, 1997, discloses intermediates useful for preparation of 6-O-methyl 3-descladinose erythromycin derivatives. U.S. Pat. No. 5,631,355 discloses certain tricyclic 6-O-methyl 3-oxo erythromycin derivatives. U.S. Pat. No. 5,527,780 discloses certain bicyclic 6-O-methyl-3-oxo erythromycin A derivatives (Agouridas, ROUSSEL) corresponding to EP application 596802, published May 11, 1994. U.S. Pat. Nos. 5,866,549 and 6,075,011, and PCT application WO 00/78773, published Dec. 28, 2000, disclose certain 6-O-substituted erythromycin derivatives. U.S. Pat. No. 6,124,269 and PCT application WO 00/62783, published Oct. 26, 2000, disclose certain 2-halo-6-O-substituted ketolide derivatives. U.S. Pat. No. 6,046,171 and PCT application WO 99/21864, published May 6, 1999, disclose certain 6,11-bridged erythromycin derivatives.

PCT Application WO 03/095466 A1, published Nov. 20, 2003 and PCT Application WO 03/097659 A1, published Nov. 27, 2003 disclose a series of bicyclic erythromycin derivatives.

SUMMARY OF THE INVENTION

The present invention provides a novel class of C6-C11 bridged oxime erythromycin derivatives which possess antibacterial activity.

In one aspect of the present invention there are provided novel bridged erythromycin compounds represented by the formulae as illustrated below:

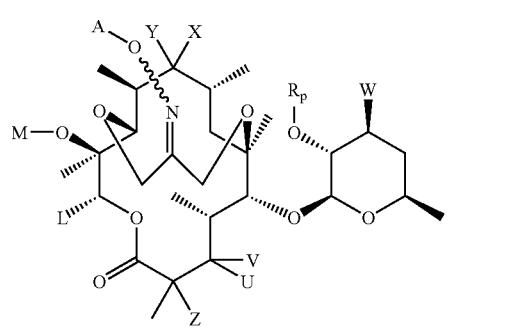

I or their racemates, enantiomers, regioisomers, salts, esters or prodrugs thereof, wherein X and Y are independently selected from the group consisting of: hydrogen, deuterium, halogen, $R_1$, $OR_1$, $S(O)_nR_1$, —$NR_1C(O)R_2$, —$NR_1C(O)NR_3R_4$, —$NR_1S(O)_nR_2$, —$C(O)NR_3R_4$, and —$NR_3R_4$;

Each of $R_1$ and $R_2$ is independently selected from the group consisting of: hydrogen, acyl, silane, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group;

Each of $R_3$ and $R_4$ is independently selected from the group consisting of: hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, a substituted, or unsubstituted heterocyclic group; or can be taken together with the nitrogen atom to which they are attached to form a substituted or unsubstituted heterocyclic or heteroaromatic ring;

or X and Y, taken together with the carbon atom to which they are attached, are selected from the group consisting of: CO, C=$CHR_1$, C=$NR_1$, C=$NC(O)R_1$, C=$NOR_1$, C=NO$(CH_2)_mR_1$, C=$NNHR_1$, C=$NNHCOR_1$, C=$NNHCONR_1R_2$, C=$NNHS(O)_nR_1$, C=N—N=$CHR_1$, C=N—$NO_2$, or C=N—ONO;

one of U or V is hydrogen and the other is independently selected from the group consisting of: $R_1$, $OR_1$, $OC(O)R_1$, $OC(O)NR_3R_4$, $S(O)_nR_1$,

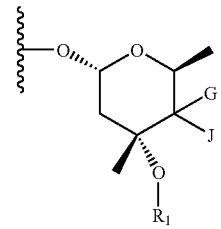

or U and V, taken together with the carbon atom to which they are attached, are C=O;

one of J or G is hydrogen and the other is selected from: $R_1$, $OR_1$, or $NR_3R_4$;

or, J and G, taken together with the carbon atom to which they are attached, are selected from: C=O, C=NR$_1$, C=NOR$_1$, C=NO(CH$_2$)$_m$R$_1$, C=NNHR$_1$, C=NNHCOR$_1$, C=NNHCONR$_1$R$_2$, C=NNHS(O)$_n$R$_1$, or C=N—N=CHR$_1$;

L is selected from the group consisting of: hydrogen, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group;

M is $R_1$;

W is $NR_3R_4$;

Z is hydrogen, alkyl or halogen;

$R_p$ is hydrogen, hydroxy protecting group or hydroxy prodrug group;

m is an integer; and n is 0, 1, or 2.

A is

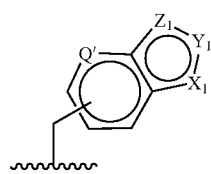

wherein:

Q' is N, CH or CF;

$X_1$ is O, N, $NR_1$, S, or $CR_5$;

$Y_1$ is O, N, $NR_1$, S, $CR_5$, or Se;

$Z_1$ is O, N, $NR_1$, S, or $CR_5$;

$R_5$ is independently selected from hydrogen, acyl, silane, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, a substituted or unsubstituted heterocyclic group, $NR_3R_4$, OH, $NHCOR_1$ or $NHCONH_2$, and is preferably, $NH_2$ or $NHR_1$.

With the proviso that a compound of Formula I is not selected from compound having the following formula where A, Q, and Z as defined below in the table A.

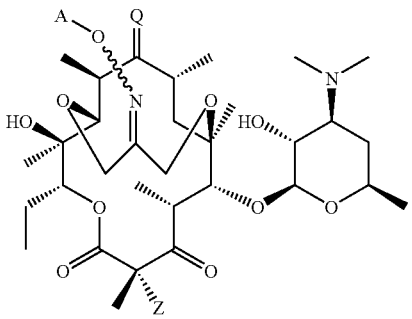

TABLE A

| Compound | A | Q | Z |
|---|---|---|---|
| 01 | 7-azaindole-CH₂- | NAc | H |
| 02 | indazole-CH₂- | NAc | H |
| 03 | indazole-CH₂- | NH | H |
| 04 | 2-amino-benzothiazole-CH₂- | NAc | H |

In one preferred embodiment, A is:

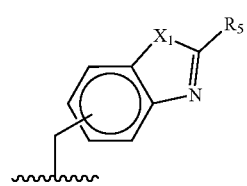

wherein $X_1$, and $R_5$ is as defined previously.

In another preferred embodiment, A is:

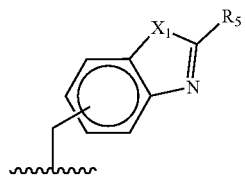

wherein $X_1$ is O, NH or S, and $R_5$ is as defined previously.

In yet another embodiment, A is:

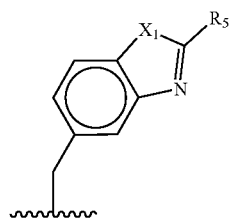

wherein $X_1$ is O, NH or S, and $R_5$ is as defined previously.

In yet another embodiment, A is:

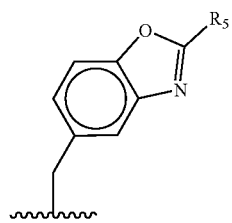

wherein $R_5$ is as defined previously.

In yet another embodiment, A is:

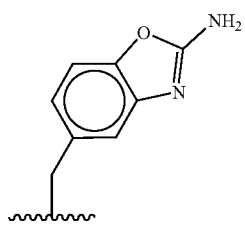

In one preferred embodiment, A is selected from the compounds shown in Table B.

TABLE B

| Number | A- |
|---|---|
| 01 | |
| 02 | |
| 03 | |
| 04 | |
| 05 | |
| 06 | |
| 07 | |
| 08 | |
| 09 | |
| 10 | |

TABLE B-continued
| Number | A- |
|---|---|
| 11 | 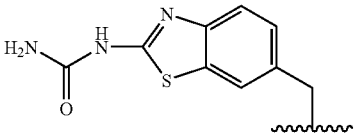 |
| 12 | 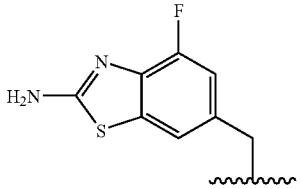 |
| 13 | 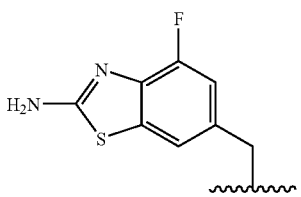 |
| 14 | 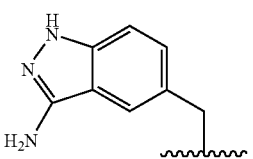 |
| 15 | 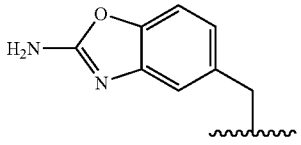 |
| 16 | 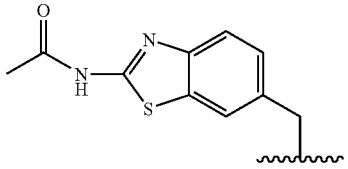 |
| 17 | 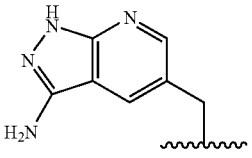 |
| 18 | 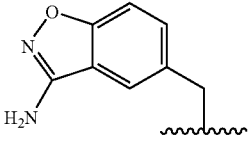 |
| 19 | 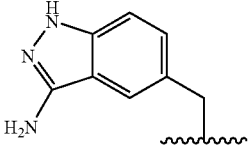 |
| 20 | 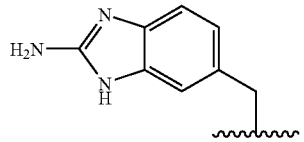 |
| 21 | 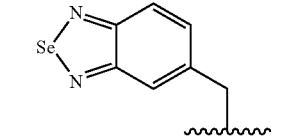 |
| 22 | 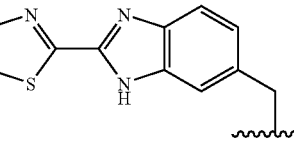 |
| 23 | 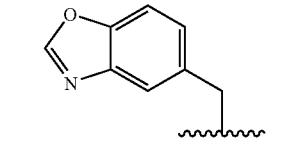 |
| 24 | 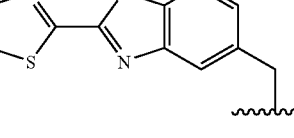 |
| 25 | 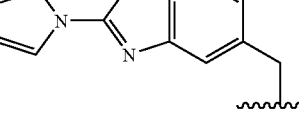 |
| 26 | 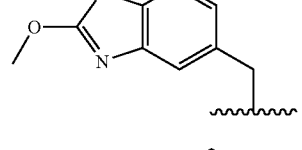 |
| 27 | 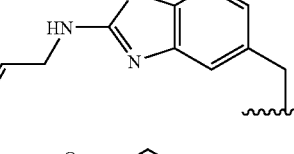 |
| 28 | 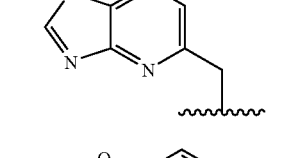 |
| 29 | 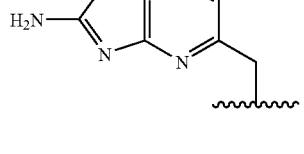 |

TABLE B-continued

| Number | A- |
|---|---|
| 30 | (N,N-diallyl-benzoxazol-2-amine, linked via benzene) |
| 31 | (1H-benzotriazole, linked via benzene) |
| 32 | (1-methyl-benzotriazole, linked via benzene) |
| 33 | (2-amino-benzoxazole, linked via benzene) |

One preferred compound of the invention has the formula II:

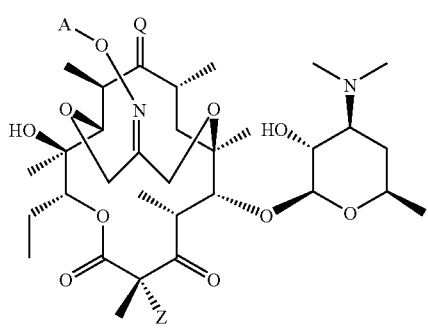

Where in A, Q, and Z are as defined in Table C:

TABLE C

| Number | A | Q | Z |
|---|---|---|---|
| 01 | benzothiazole (6-linked) | NAc | H |
| 02 | 2-amino-benzothiazole (6-linked) | NAc | F |
| 03 | 2,1,3-benzothiadiazole | NAc | H |
| 04 | 2-amino-benzothiazole (5-linked) | NAc | H |
| 05 | benzoxazole | NAc | H |
| 06 | 3-amino-benzisoxazole (5-linked) | NAc | H |
| 07 | 3-amino-benzisoxazole (6-linked) | NAc | H |
| 08 | 2-amino-benzoxazole (6-linked, F) | NAc | F |
| 09 | 2-amino-benzothiazole | O | H |
| 10 | 2-amino-benzoxazole | NAc | H |

TABLE C-continued

| Number | A | Q | Z |
|--------|---|---|---|
| 11 | 2-aminobenzoxazol-6-yl | O | H |
| 12 | 2-(ureido)benzothiazol-6-yl | NAc | H |
| 13 | 2-amino-4-fluorobenzothiazol-6-yl | NAc | H |
| 14 | 2-(ureido)benzothiazol-6-yl | O | H |
| 15 | 2-amino-4-fluorobenzothiazol-6-yl | O | H |
| 16 | 3-amino-1H-indazol-5-yl | NAc | H |
| 17 | 2-aminobenzoxazol-5-yl | NAc | H |
| 18 | 2-aminobenzoxazol-5-yl | O | H |
| 19 | 2-(acetylamino)benzothiazol-6-yl | NAc | H |
| 20 | 3-amino-1H-pyrazolo[3,4-b]pyridin-5-yl | NAc | H |
| 21 | 3-aminobenzisoxazol-5-yl | NAc | F |
| 22 | 3-amino-1H-indazol-5-yl | NAc | F |
| 23 | 2-amino-1H-benzimidazol-5-yl | NAc | H |
| 24 | 2-amino-1H-benzimidazol-5-yl | O | H |
| 25 | 2,1,3-benzoselenadiazol-5-yl | NAc | H |
| 26 | 2-(thiazol-2-yl)-1H-benzimidazol-5-yl | NAc | H |
| 27 | benzoxazol-5-yl | NAc | H |
| 28 | benzoxazol-5-yl | O | H |
| 29 | 2-(thiazol-2-yl)benzoxazol-5-yl | NAc | H |

TABLE C-continued

| Number | A | Q | Z |
|---|---|---|---|
| 30 | (pyrazol-1-yl-benzoxazol-5-ylmethyl) | NAc | H |
| 31 | (2-methoxy-benzoxazol-5-ylmethyl) | NAc | H |
| 32 | (2-allylamino-benzoxazol-5-ylmethyl) | NAc | H |
| 33 | (oxazolo[4,5-b]pyridin-5-ylmethyl) | NAc | H |
| 34 | (2-amino-oxazolo[4,5-b]pyridin-5-ylmethyl) | NAc | H |
| 35 | (2-diallylamino-benzoxazol-5-ylmethyl) | NAc | H |
| 36 | (1H-benzotriazol-5-ylmethyl) | NAc | H |
| 37 | (1-methyl-benzotriazol-5-ylmethyl) | NAc | H |
| 38 | (2-amino-benzoxazol-5-ylmethyl) | NC(O)OCH$_3$ | H |
| 39 | (2-amino-benzoxazol-5-ylmethyl) | NH | H |

One preferred compound of the invention has the formula III:

III wherein $R_p$, U, V, W, X, Y, L, and Z are as defined previously.

Another preferred compound of the invention has the formula IV:

IV wherein Z and $R_p$ are as previously defined.

Yet another preferred compound of the invention has the formula V:

V

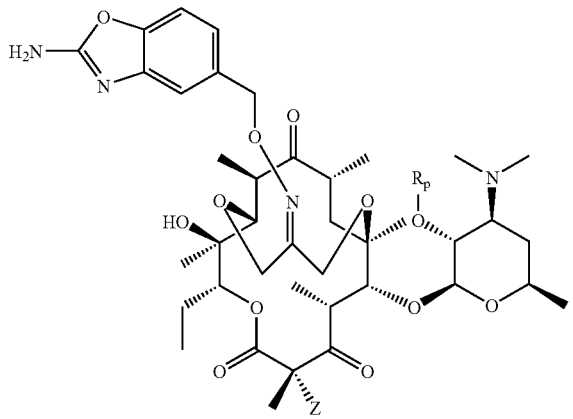

wherein Z and $R_p$ are as defined previously.

In another aspect of the invention, there are provided novel 3-acylide bridged erythromycin compounds represented by the Formula VI:

VI

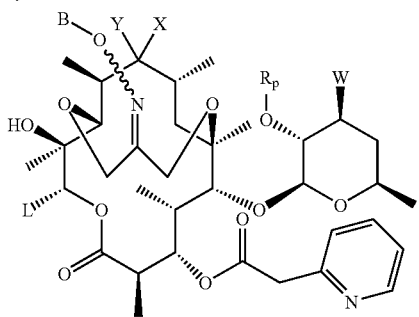

or any racemates, enantiomers, regioisomers, salts, esters, or prodrugs thereof wherein X, Y, L, W, and $R_p$ are as defined previously;

B is independently selected from hydrogen, acyl, silane, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group.

One preferred compound of Formula VI has the formula VII:

VII

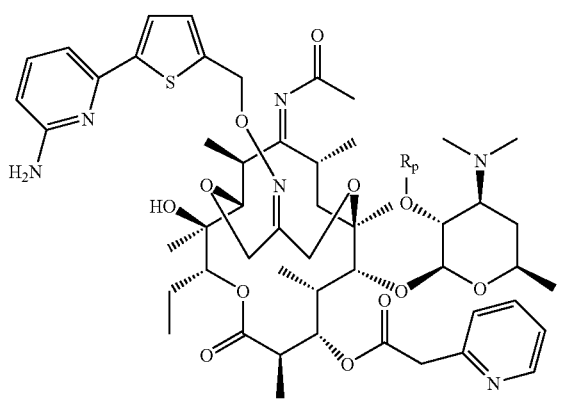

wherein $R_p$ is as previously defined.

DETAILED DESCRIPTION OF THE INVENTION

Definitions

Listed below are definitions of various terms used to describe this invention. These definitions apply to the terms as they are used throughout this specification and claims, unless otherwise limited in specific instances, either individually or as part of a larger group.

An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The terms "$C_1$-$C_3$ alkyl," "$C_1$-$C_6$ alkyl," or "$C_1$-$C_{12}$ alkyl," as used herein, refer to saturated, straight- or branched-chain hydrocarbon radicals containing between one and three, one and twelve, or one and six carbon atoms, respectively. Examples of $C_1$-$C_3$ alkyl radicals include methyl, ethyl, propyl and isopropyl radicals; examples of $C_1$-$C_6$ alkyl radicals include, but are not limited to, methyl, ethyl, propyl, propyl, butyl, pentyl, and hexyl radicals; and examples of $C_1$-$C_{12}$ alkyl radicals include, but are not limited to, ethyl, propyl, propyl, hexyl, heptyl, octyl, nonyl, decyl, undecyl, dodecyl radicals and the like.

The term "substituted alkyl," as used herein, refers to an alkyl, such as a $C_1$-$C_{12}$ alkyl or $C_1$-$C_6$ alkyl group, substituted by one, two, three or more aliphatic or aromatic substituents.

Suitable aliphatic or aromatic substituents include, but are not limited to, —F, —Cl, —Br, —I, —OH, protected hydroxy, aliphatic ethers, aromatic ethers, oxo, —NO$_2$, —CN, —$C_1$-$C_{12}$-alkyl optionally substituted with halogen (such as perhaloalkyls), $C_2$-$C_{12}$-alkenyl optionally substituted with halogen, —$C_2$-$C_{12}$-alkynyl optionally substituted with halogen, —NH$_2$, protected amino, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —CO$_2$—$C_1$-$C_{12}$-alkyl, —CO$_2$—$C_2$-$C_{12}$-alkenyl, —CO$_2$—$C_2$-$C_{12}$-alkynyl, —CO$_2$—$C_3$-$C_{12}$-cycloalkyl, —CO$_2$-aryl, —CO$_2$-heteroaryl, —CO$_2$-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkynyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH-aryl, —OCONH-heteroaryl, —OCONH— heterocycloalkyl, —NHC(O)—C$_1$-C$_{12}$-alkyl, —NHC(O)—C$_2$-C$_{12}$-alkenyl, —NHC(O)—C$_2$-C$_{12}$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$-C$_{12}$-alkyl, —NHC(O)NH—C$_2$-C$_{12}$-alkenyl, —NHC(O)NH—C$_2$-C$_{12}$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$-C$_{12}$-alkyl, —NHC(S)NH—C$_2$-C$_{12}$-alkenyl, —NHC(S)NH—C$_2$-C$_{12}$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(O)NH$_2$, NHC(NH)NH—C$_1$-C$_{12}$-alkyl, —NHC(NH)NH—C$_2$-C$_{12}$-alkenyl, —NHC(NH)NH—C$_2$-C$_{12}$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, NHC(NH)—C$_1$-C$_{12}$-alkyl, —NHC(NH)—C$_2$-C$_{12}$-alkenyl, —NHC(NH)—C$_2$-C$_{12}$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkynyl, —S(O)—C$_3$-C$_{12}$-cycloalkyl, —S(O)-aryl, —S(O)-heteroaryl, —S(O)-heterocycloalkyl-SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkynyl, —S—C$_3$-C$_{12}$-cycloalkyl, —S-aryl, —S-heteroaryl, —S-heterocycloalkyl, or methylthiomethyl. It is understood that the aryls, heteroaryls, alkyls and the like can be further substituted.

The terms "C$_2$-C$_{12}$ alkenyl" or "C$_2$-C$_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, alkadienes and the like.

The term "substituted alkenyl," as used herein, refers to a "C$_2$-C$_{12}$ alkenyl" or "C$_2$-C$_6$ alkenyl" group as previously defined, substituted by one, two, three or more aliphatic substituents.

The terms "C$_2$-C$_{12}$ alkynyl" or "C$_2$-C$_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "C$_2$-C$_{12}$ alkynyl" or "C$_2$-C$_6$ alkynyl" group as previously defined, substituted by one, two, three or more aliphatic substituents.

The term "C$_1$-C$_6$ alkoxy," as used herein, refers to a C$_1$-C$_6$ alkyl group, as previously defined, attached to the parent molecular moiety through an oxygen atom. Examples of C$_1$-C$_6$-alkoxy include, but are not limited to, methoxy, ethoxy, propoxy, isopropoxy, n-butoxy, sec-butoxy, tert-butoxy, n-pentoxy, neopentoxy and n-hexoxy.

The terms "halo" and "halogen," as used herein, refer to an atom selected from fluorine, chlorine, bromine and iodine.

The terms "aryl" or "aromatic," as used herein, refer to a mono- or bicyclic carbocyclic ring system having one or two aromatic rings including, but not limited to, phenyl, naphthyl, tetrahydronaphthyl, indanyl, idenyl and the like.

The terms "substituted aryl" or "substituted aromatic," as used herein, refer to an aryl group, as previously defined, substituted by one, two, three or more aromatic substituents.

The term "arylalkyl," as used herein, refers to an aryl group attached to the parent compound via a C$_1$-C$_3$ alkyl or C$_1$-C$_6$ alkyl residue. Examples include, but are not limited to, benzyl, phenethyl and the like.

The term "substituted arylalkyl," as used herein, refers to an arylalkyl group, as previously defined, substituted by one, two, three or more aromatic substituents.

The terms "heteroaryl" or "heteroaromatic," as used herein, refers to a mono-, bi-, or tri-cyclic aromatic radical or ring having from five to ten ring atoms of which at least one ring atom is selected from S, O and N; zero, one, two, three or more ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, tetrazolyl and the like. The heteroaromatic ring may be bonded to the chemical structure through a carbon or hetero atom.

The terms "substituted heteroaryl" or "substituted heteroaromatic," as used herein, refer to a heteroaryl group as previously defined, substituted by one, two, three or four aromatic substituents.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl.

The term "substituted alicyclic" group as previously defined, substituted by one, two, three or more aliphatic substituents.

The terms "heterocyclic" as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl, and the like.

The term "substituted heterocyclic," as used herein, refers to a heterocyclic group, as previously defined, substituted by one, two, three or more aliphatic substituents.

The term "heteroarylalkyl," as used herein, refers to a heteroaryl group attached to the parent compound via a $C_1$-$C_3$ alkyl or $C_1$-$C_6$ alkyl residue. Examples include, but are not limited to, pyridinylmethyl, pyrimidinylethyl and the like.

The term "substituted heteroarylalkyl," as used herein, refers to a heteroarylalkyl group, as previously defined, substituted by independent replacement of one, two, or three or more aromatic substituents.

The term "$C_1$-$C_3$-alkylamino," as used herein, refers to one or two $C_1$-$C_3$-alkyl groups, as previously defined, attached to the parent molecular moiety through a nitrogen atom. Examples of $C_1$-$C_3$-alkylamino include, but are not limited to, methylamino, dimethylamino, ethylamino, diethylamino, and propylamino.

The term "alkylamino" refers to a group having the structure —NH($C_1$-$C_{12}$ alkyl) where $C_1$-$C_{12}$ alkyl is as previously defined.

The term "dialkylamino" refers to a group having the structure —N($C_1$-$C_{12}$ alkyl) ($C_1$-$C_{12}$ alkyl), where $C_1$-$C_{12}$ alkyl is as previously defined. Examples of dialkylamino are, but not limited to, dimethylamino, diethylamino, methylethylamino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH($C_1$-$C_{12}$ alkyl) or —C(O)N($C_1$-$C_{12}$ alkyl) ($C_1$-$C_{12}$ alkyl), —C(O)NH$_2$, —NHC(O)($C_1$-$C_{12}$ alkyl), —N($C_1$-$C_{12}$ alkyl)C(O)($C_1$-$C_{12}$ alkyl) and the like.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl(Ac or —C(O)CH$_3$), benzoyl(Bz or —C(O)C$_6$H$_5$), and trimethylsilyl(TMS or —Si(CH$_3$)$_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

The term "protogenic organic solvent" or "protic solvent," as used herein, refers to a solvent that tends to provide protons, such as an alcohol, for example, methanol, ethanol, propanol, isopropanol, butanol, t-butanol, water and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)— or (S)—, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers Racemates and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating bacterial infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

As used herein, unless otherwise indicated, the term "bacterial infection(s)" or "protozoa infections"; includes, but is not limited to, bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include, but are not limited to, the following: pneumonia, otitis media, sinusitus, bronchitis, tonsillitis, cystic fibrosis (CF) and mastoiditis related to infection by *Streptococcus pneumoniae, Haemophilus influenzae, Moraxella catarrhalis, Staphylococcus aureus, Peptostreptococcus* spp. or *Pseudomonas* spp.; pharynigitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *S. pyogenes, S. agalactiae*, Streptococcal groups C—F (minute-colony streptococci), viridans streptococci, *Corynebacterium* spp., *Clostridium* spp., or *Bartonella henselae*; uncomplicated acute urinary tract infections related to infection by *S. saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum*, or *Nesseria gonorrheae*; toxin diseases related to infection by *S. aureus* (food poisoning and Toxic shock syndrome), or Groups A, S. and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; tuberculosis disease related to infection by *Mycobacterium tuberculosis*; gastroenteritis related to infection by *Campylobacter jejuni*; intestinal protozoa related to infection by *Cryptosporidium* spp. odontogenic infection related to infection by viridans streptococci; persistent cough related to infection by *Bordetella pertussis*; gas gangrene related to infection by *Clostridium perfringens* or *Bacteroides* spp.; Skin infection by *S. aureus, Propionibacterium acne*; atherosclerosis related to infection by *Helicobacter pylori* or *Chlamydia pneumoniae*; or the like.

Bacterial infections and protozoa infections and disorders related to such infections that may be treated or prevented in animals include, but are not limited to, the following: bovine respiratory disease related to infection by *P. haemolytica., P. multocida, Mycoplasma bovis*, or *Bordetella* spp.; cow enteric disease related to infection by *E. coli* or protozoa (i.e., coccidia, cryptosporidia, etc.), dairy cow mastitis related to infection by *S. aureus, S. uberis, S. agalactiae, S. dysgalactiae, Klebsiella* spp., *Corynebacterium*, or *Enterococcus* spp.; swine respiratory disease related to infection by *A. pleuropneumoniae., P. multocida*, or *Mycoplasma* spp.; swine enteric disease related to infection by *E. coli, Lawsonia intracellularis, Salmonella* spp., or *Serpulina hyodyisinteriae*; cow footrot related to infection by *Fusobacterium* spp.; cow metritis related to infection by *E. coli*; cow hairy warts related to Infection by *Fusobacterium necrophorum* or *Bacteroides nodosus*; cow pink-eye related to infection by *Moraxella bovis*, cow premature abortion related to infection by protozoa (i.e. neosporium); urinary tract infection in dogs and cats related to infection by *E. coli*; skin and soft tissue infections in dogs and cats related to infection by *S. epidermidis, S. intermedius*, coagulase neg. *Staphylococcus* or *P. multocida*; and dental or mouth infections in dogs and oats related to infection by *Alcaligenes* spp., *Bacteroides* spp., *Clostridium* spp., *Enterobacter* spp., *Eubacterium* spp.,

*Peptostreptococcus* spp., *Porphfyromonas* spp., *Campylobacter* spp., *Actinomyces* spp., *Erysipelothrix* spp., *Rhodococcus* spp., *Trypanosoma* spp., *Plasmodium* spp., *Babesia* spp., *Toxoplasma* spp., *Pneumocystis* spp., *Leishmania* spp., and *Trichomonas* spp. or *Prevotella* spp. Other bacterial infections and protozoa infections and disorders related to such infections that may be treated or prevented in accord with the method of the present invention are referred to in J. P. Sanford at al., "The Sanford Guide To Antimicrobial Therapy," 26th Edition, (Antimicrobial Therapy, Inc., 1996).

Antibacterial activity studies may be carried out using suitable assays as are known in the art. Susceptibility tests can be used to quantitatively measure the in vitro activity of an antimicrobial agent against a given bacterial isolate. Compounds are tested for in vitro antibacterial activity by a micro-dilution method. Minimal Inhibitory Concentration (MIC) is determined in 96 well microtiter plates utilizing the appropriate Mueller Hinton Broth medium (CAMHB) for the observed bacterial isolates. Antimicrobial agents are serially diluted (2-fold) in DMSO to produce a concentration range from about 64 µg/ml to about 0.03 µg/ml. The diluted compounds (2 µl/well) are then transferred into sterile, uninoculated CAMHB (0.2 mL) by use of a 96 fixed tip-pipeting station. The inoculum for each bacterial strain is standardized to $5 \times 10^5$ CFU/mL by optical comparison to a 0.5 McFarland turbidity standard. The plates are inoculated with 10 µl/well of adjusted bacterial inoculum. The 96 well plates are covered and incubated at 35+/−2° C. for 24 hours in ambient air environment. Following incubation, plate wells are visually examined by Optical Density measurement for the presence of growth (turbidity). The lowest concentration of an antimicrobial agent at which no visible growth occurs is defined as the MIC. The compounds of the invention generally demonstrated an MIC in the range from about 64 µg/ml to about 0.03 µg/ml.

All in vitro testing follows the guidelines described in the Approved Standards M7-A4 protocol, published by the National Committee for Clinical Laboratory Standards (NC-CLS).

The invention further provides compositions and methods of treating subjects suffering from an inflammatory condition comprising administering to a subject in need thereof, a therapeutically effective amount of at least one compound of the invention. Specific examples of inflammatory conditions treatable according to the invention include, but are not limited to, scleritis; epi-scleritis; allergic conjunctivitis; pulmonary inflammatory diseases, particularly CF, asthma, chronic obstructive pulmonary disease (COPD), allergic bronchopulmonary aspergillosis (ABPA), and sarcoidosis; procto-sigmoiditis; allergic rhinitis; arthritis; tendonitis; apthous stomatitis; and inflammatory bowel disease.

The invention further provides compositions and methods for i) prophylactic treatment of those subjects susceptible to the symptoms CF including pulmonary infection and inflammation associated with CF, ii) treatment at the initial onset of symptoms of pulmonary infection and inflammation associated with CF, and iii) treatment of ongoing or relapsing symptoms of infection and inflammation associated with CF. In accordance with the invention a compound of the invention, is administered to a subject in need of treatment for CF, in amount sufficient to prevent, diminish or eradicate symptoms of CF including chronic pulmonary inflammation and infection.

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the subject in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43,650 by Montgomery, all of which are incorporated herein by reference). A discussion of pulmonary delivery of antibiotics is also found in U.S. Pat. No. 6,014,969, incorporated herein by reference.

According to the methods of treatment of the present invention, bacterial infections, cystic fibrosis and inflammatory conditions are treated or prevented in a subject such as a human or another animal by administering to the subject a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a subject in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The pharmaceutical compositions of this invention can be administered orally to fish by blending said pharmaceutical compositions into fish feed or said pharmaceutical compositions may be dissolved in water in which infected fish are placed, a method commonly referred to as a medicated bath. The dosage for the treatment of fish differs depending upon the purpose of administration (prevention or cure of disease) and type of administration, size and extent of infection of the fish to be treated. Generally, a dosage of 5-1000 mg, preferably 20-100 mg, per kg of body weight of fish may be administered per day, either at one time or divided into several times. It will be recognized that the above-specified dosage is only a general range which may be reduced or increased depending upon the age, body weight, condition of disease, etc. of the fish.

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may be used in the descriptions of the scheme and the examples that follow are:

Ac for acetyl;
AIBN for azobisisobutyronitrile;
$Bu_3SnH$ for tributyltin hydride;
CDI for carbonyldiimidazole;
dba for dibenzylidene acetone;
dppb for diphenylphosphino butane;
DBU for 1,8-diazabicyclo[5.4.0]undec-7-ene;
DEAD for diethylazodicarboxylate;
DMAP for dimethylaminopyridine;
DMF for dimethyl formamide;
DPPA for diphenylphosphoryl azide;
EtOAc for ethyl acetate;
EtOH for ethanol;
MeOH for methanol;
Ms for mesylate or $O-SO_2-CF_3$;
$NaN(TMS)_2$ for sodium bis(trimethylsilyl)amide;
NMMO for N-methylmorpholine N-oxide;
TEA for triethylamine;
THF for tetrahydrofuran;
TPP or $PPh_3$ for triphenylphosphine;
MOM for methoxymethyl;
Boc for t-butoxycarbonyl;
Bz for benzoyl;
Bn for benzyl;
Ph for phenyl;
POPd for dihydrogen dichlorobis(di-tert-butylphosphinito-κP)palladate(II);
TBS for tert-butyl dimethylsilyl; or
TMS for trimethylsilyl.

Synthetic Methods

The compounds and processes of the present invention will be better understood in connection with the following synthetic schemes that illustrate the methods by which the compounds of the invention may be prepared.

A preferred intermediate for the preparation of compounds represented by formula I is a compound represented by formula VIII as illustrated below

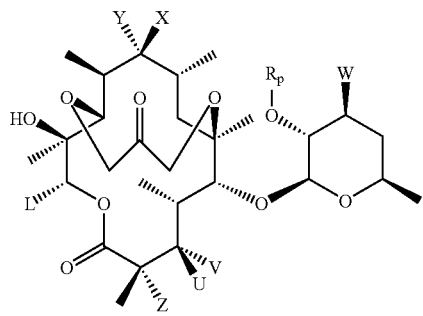

VIII wherein $R_p$, U, V, W, X, Y and Z are as previously defined.

Schemes 1-2 describe processes for the preparation of compounds according to the invention.

Compounds of formula VIII, which are useful as the starting materials for the preparation of compounds of the present invention are prepared from erythromycin using the procedures described in U.S. Pat. No. 6,878,691 and U.S. Patent Application Publication No. 2004/0053861, incorporated herein by reference.

Scheme 1

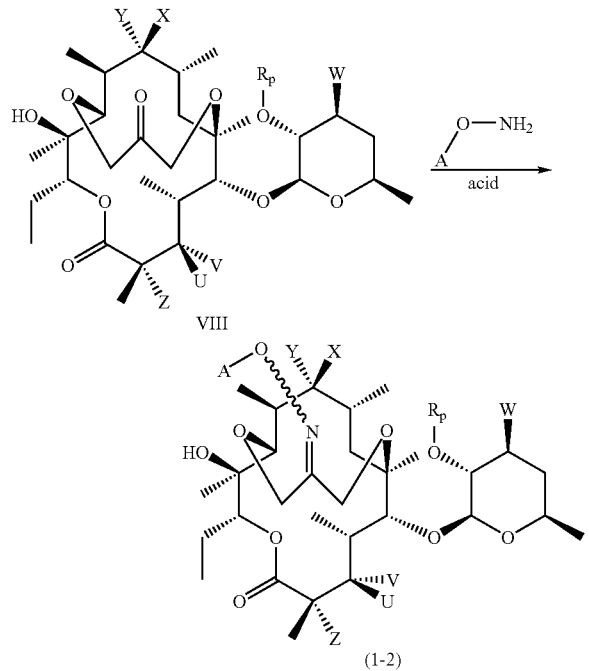

Scheme 1 illustrates a process of preparing compounds of the present invention by converting the bridged ketone of VIII into an oxime of formula (1-2) using the appropriate substituted hydroxylamine of the formula:

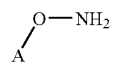

where A is as previously defined. This oxime formation can be accomplished, using the appropriate substituted hydroxylamine under either acidic or basic conditions in a variety of solvents. Representative acids include, but are not limited to, hydrochloric acid, phosphoric acid, sulfuric acid, p-toluenesulfonic acid, and pyridinium p-toluene sulfonate and the likes. Likewise, representative bases include, but are not limited to, triethylamine, pyridine, diisopropylethyl amine, 2,6-lutidine, and the likes. Appropriate solvents include, but are not limited to, methanol, ethanol, water, tetrahydrofuran, 1,2-dimethoxyethane, ethyl acetate and the likes. Preferably the reaction is carried out in ethanol using aqueous hydrochloric acid. Reaction temperature is generally, but not limited to, from −20° C. to 40° C. and the reaction time is from 1 to 8 hours, preferably the reaction is carried out at 0° C.

Scheme 2

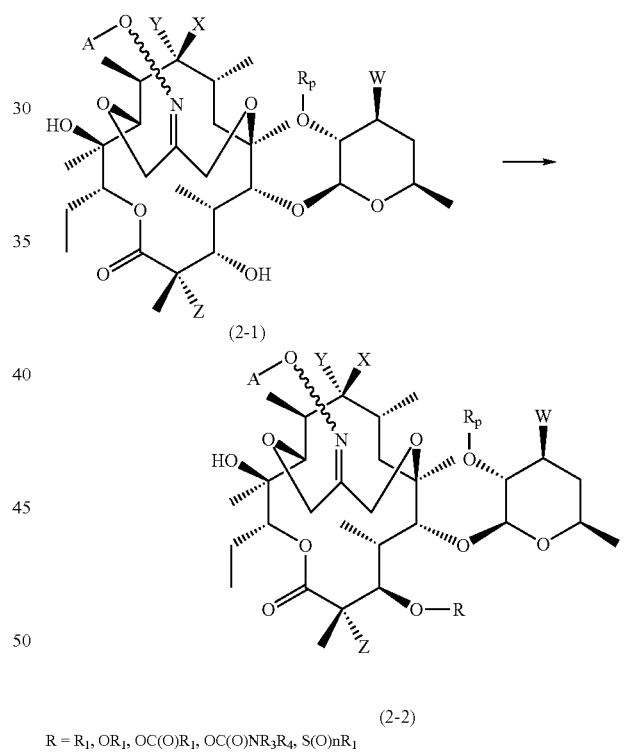

R = $R_1$, $OR_1$, $OC(O)R_1$, $OC(O)NR_3R_4$, $S(O)nR_1$

Scheme 2 illustrates the procedure by which compounds of formula (2-1) may be converted to compounds of formula (2-2) by treatment with isocyanates of formula R1-NCO, acid chlorides of formula R1-C(O)Cl or Alkyl isocyanates in the present of bases such as, but not limited to, sodium hydride, potassium hydride, potassium tert-butoxide, potassium hydroxide, KHMDS, and the like. The reaction is typically carried out in aprotic solvents such as, but not limited to, THF, DMSO, DMF, or dioxane and the likes. The temperature of the reaction is from 25° C. to 80° C. The preferred reaction time is from 5 to 20 hours.

Alternatively, some of the ester compounds of formula (2-2) can be prepared by treating compounds of formula (2-1) with acids of formula R1-C(O)OH in the presence of bases such as but not limited to Et$_3$N, Pyridine, DMAP and coupling agents such as but not limited to EDC, BOPCl, HATU, and the likes in aprotic solvents such as but not limited to dichloromethane, ethylene chloride, THF, DMF, acetonitrile and the like at a temperature from 25° C. to 80° C. and the reaction time is from 2 to 24 hours.

Compounds of formula (2-1) also can be treated with with substituted tert-butyl allyl carbonate in the presence of a palladium catalyst and a phosphine additive to give allyl ethers.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

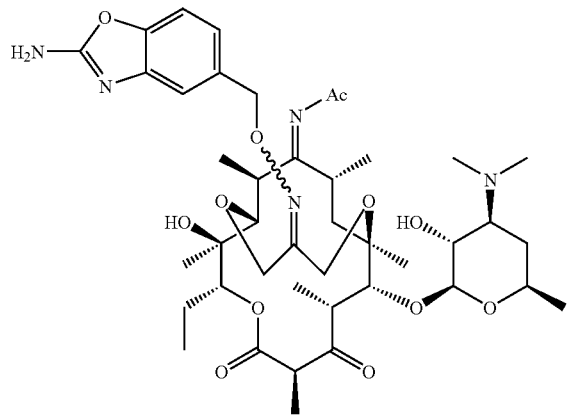

Step 1a:

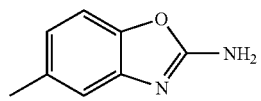

To a solution of 2-amino-4-methylphenol (157.6 g, 1.28 mol) in 1500 ml of EtOH at room temperature, under stirred condition, was added bromocyanogen (135.00 g, 1.28 mol) in about 30 minutes. During the addition, the reaction mixture became warm and water bath was used to cool the reaction to room temperature. After 5-6 hours, the reaction solvent was evaporated under reduced pressure. The residue was dissolved in about 1500 ml of EtOAc and washed with the saturated NaHCO$_3$ (1.5 L). The organic layer was separated and dried over anhydrous MgSO$_4$. Removal of solvent and dried by high vacuum gave about 150 g of the title compound as pale brown color, which can be used in next step. ESI MS m/e: 149 (M+H)$^+$.

Step 1b:

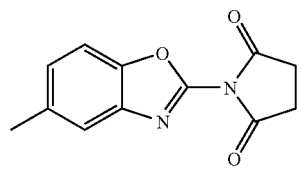

A solution of succinic anhydride (141.1 g, 1.41 mol) and 70 g (about 0.47 mol) of compound of step 1a (70 g, 0.47 mol) in 2500 ml of anhydrous toluene was refluxed for overnight. After that, HATU (100 g, 0.26 mol) and 4-methylmorpholine (41.36 ml, 0.376 mol) were added and the resulting mixture was refluxed for 2-3 hours. TLC showed that the major spot was product (Rf=0.35, acetone:hexane=1:2). After reaction was completed, the solvent was evaporated and the residue was dissolved in about 2000 ml of CH$_2$Cl$_2$. The solution was washed with aqueous NaHCO$_3$. After pH was adjusted to 7-8 and washed with brine, organic phase was separated and dried over MgSO$_4$. Filtration and removal of solvent gave the title compound (98 g) as fine white needle crystalline ESI MS m/e: 231 (M+H)$^+$.

Step 1c:

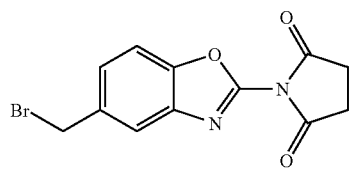

To a solution of the compound of step 1b (44.37 g, 0.193 mol) in CCl$_4$ (1.5 L) was added NBS (41.16 g, 0.23 mol) and then the mixture were heated to reflux. Benzoyl peroxide (0.75 g) was added by three times. After refluxing for 24 hours, the reaction was cooled to room temperature and the mixture was diluted with 1.5 L of CH$_2$Cl$_2$. The organic phase was separated and washed with 4 L of saturated NaHCO$_3$ two times to adjust pH to 7-8. Dried over MgSO$_4$ and removal of the solvent under reduced pressure gave the title compound (57.3 g) as slight yellow solid which was used for next step without further purification. ESI MS m/e: 309/311(M+H)$^+$.

Step 1d:

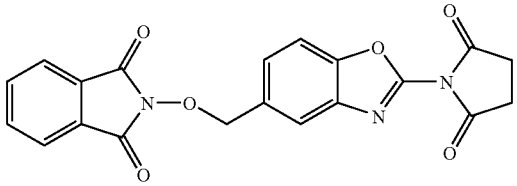

To a solution of the compound of step 1c (57.3 g, 0.185 mol) in 450 ml of MeCN were added N-hydroxyphanthalimide (60.51 g, 0.371 mol) and 80 ml of triethylamine. The reaction mixture was stirred at 50° C. for 5 hours and cooled to room temperature. The reaction was added water (200 ml) and filtered. The pale yellow solid was collected, washed with 100 ml of MeOH and ether in the 1:1 ratio. Dried on vacuum to give the title compound (48 g) as pale solid. ESI MS m/e: 392 (M+H)$^+$.

Step 1e:

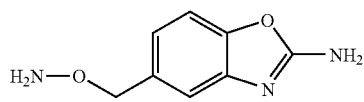

A mixture of the compound of step 1d (39.1 g, 0.1 mol) in 500 ml of 2M ammonia in methanol was stirred at room temperature for 16 hours and filtered. The filtrate was concentrated and purified on silica gel (2M NH$_3$ in MeOH:CH$_2$Cl$_2$=5:95) to give the title compound (17 g, 95%). ESI MS m/e: 180 (M+H)$^+$.

Step 1f:

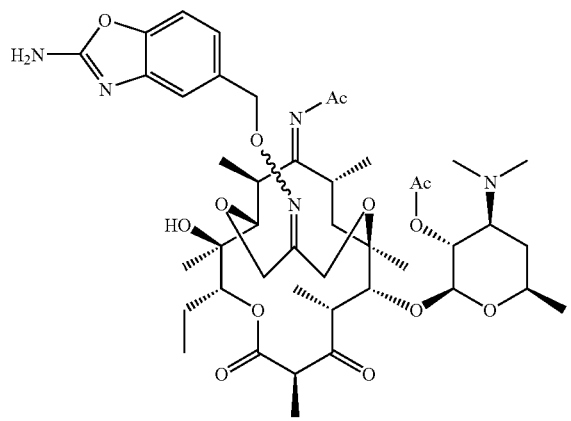

To a solution of compound of step 1 d (215 mg, 1.2 mmol) in 15 ml of ethanol was added 1N HCl (2 ml). The mixture was cooled to 0° C. and added compound of formula VIII where X and Y taken together with the atom that they are attached is C=N—Ac and U and V taken together with the atom that they are attached is C=O, Z=H, Rp=Ac and W=NMe$_2$ (711 mg, 1 mmol). The mixture was stirred at 0° C. for 1 hour and quenched with saturated NaHCO$_3$ (50 ml). Extracted with ethyl acetate (100 ml) and washed with brine (100 ml×2). Dried over anhydrous Na$_2$SO$_4$ and concentrated to give crude title compound (828 mg, 95%, as a mixture of oximes, oximeE/Z=4/1), which was used for next step reaction without further purification. ESI MS m/e: 872 (M+H)$^+$.

Step 1g:

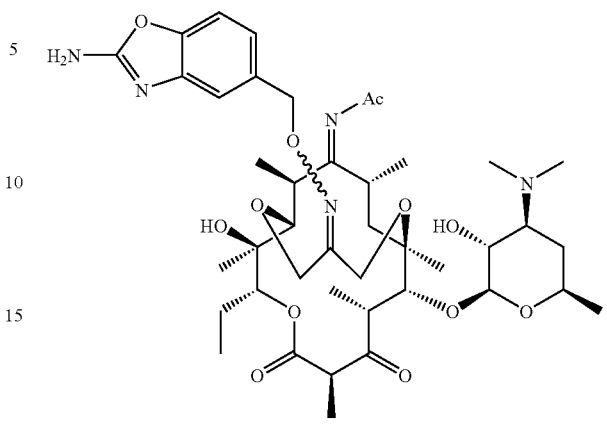

A solution of compound of step 1f (828 mg, 0.95 mmol) in 15 ml of methanol was stirred at 60° C. for 5 hours. The solvent was removed and the residue was purified on silica gel (2M NH$_3$ in MeOH/CH$_2$Cl$_2$=5/95) to give the title compound (765 mg, 97%, as a mixture of E/Z oximes E/Z ~4/1). The compound was further separated on HPLC to give E-oxime isomer (430 mg) and Z-oxime isomer (110 mg).

E-oxime isomer: ESI MS m/e: 830 (M+H)$^+$.

E-oxime isomer: $^{13}$C NMR (125 MHz, CDCl$_3$): δ 205.9, 191.4, 186.8, 184.7, 178.1, 167.8, 162.1, 153.3, 148.5, 143.0, 134.1, 125.6, 121.9, 116.8, 108.7, 103.0, 79.4, 76.4, 74.6, 70.5, 69.8, 66.1, 63.2, 62.9, 50.8, 40.5, 38.8, 31.2, 28.5, 25.3, 23.8, 21.5, 19.5, 17.8, 15.1, 14.1, 12.8.

Z-oxime isomer: ESI MS m/e: 830 (M+H)$^+$.

Z-oxime isomer: $^{13}$C NMR (125 MHz, CDCl$_3$): δ 206.2, 184.7, 176.9, 169.3, 163.0, 155.9, 148.5, 143.2, 133.6, 121.6, 116.7, 108.5, 103.0, 79.5, 79.0, 76.7, 76.2, 75.8, 70.5, 70.2, 69.7, 66.1, 58.2, 53.7, 51.0, 45.3, 40.5, 39.7, 39.0, 36.9, 28.5, 25.5, 23.4, 21.5, 20.3, 19.6, 17.3, 15.7, 14.5, 12.9, 12.0.

Example 2

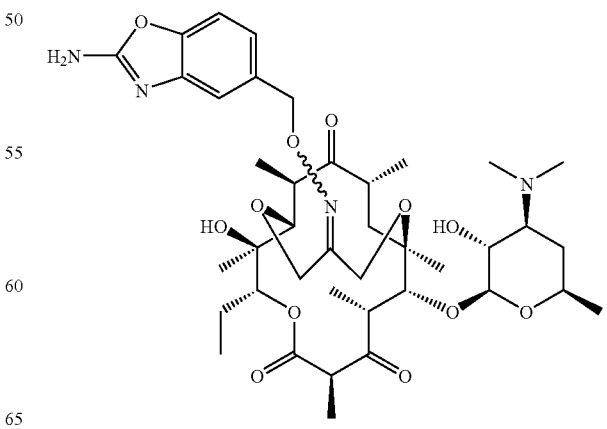

Step 2a:

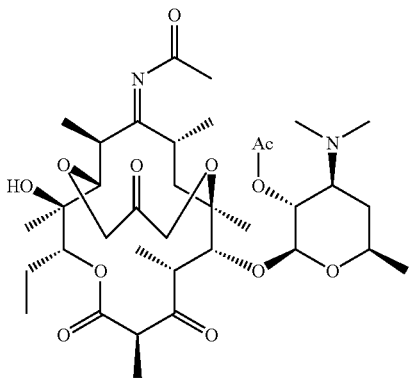

The title compound of step 2a was prepared according to experimental procedure from U.S. Pat. No. 6,878,691 incorporated herein by reference.

Step 2b:

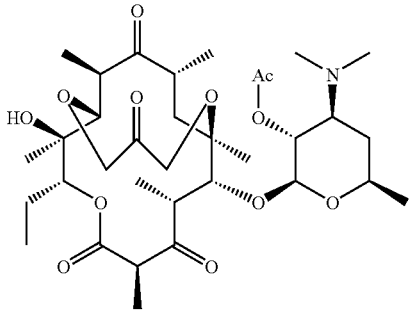

To a solution of compound of step 2a (711 mg, 1 mmol) in 8 ml of acetonitrile was added 1 N HCl (10 ml) at room temperature. The mixture was stirred at room temperature for 4 hours and was quenched with saturated NaHCO$_3$ (30 ml). Extracted with ethyl acetate (40 ml) and the organic phase was washed with brine (40 ml×2). After dried over anhydrous Na$_2$SO$_4$, the solvent was removed and the residue was purified on silica gel column (hexane:acetone=1:1) to give the title compound (330 mg, 49%).

Step 2c:

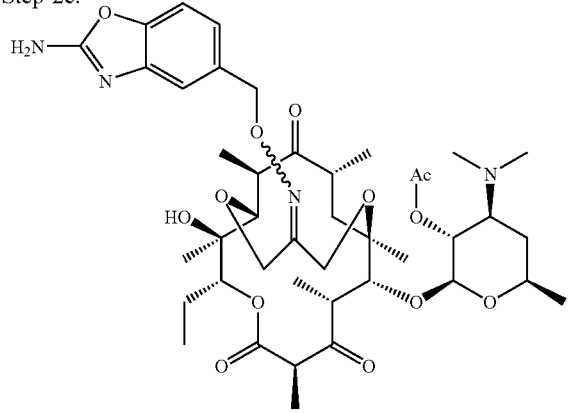

To a solution of compound from step 2b (215 mg, 1.2 mmol) in 15 ml of ethanol was added 1N HCl (2 ml). The mixture was cooled to 0° C. and added bridged ketone ketolide, compound of step 2a (670 mg, 1 mmol). The mixture was stirred at 0° C. for 1 hour and quenched with saturated NaHCO$_3$ (50 ml). Extracted with ethyl acetate (100 ml) and washed with brine (100 ml×2). Dried over anhydrous Na$_2$SO$_4$ and concentrated to give crude title compound (764 mg, 92%, E/Z ~1/1). ESI MS m/e: 831 (M+H)$^+$.

Step 2d:

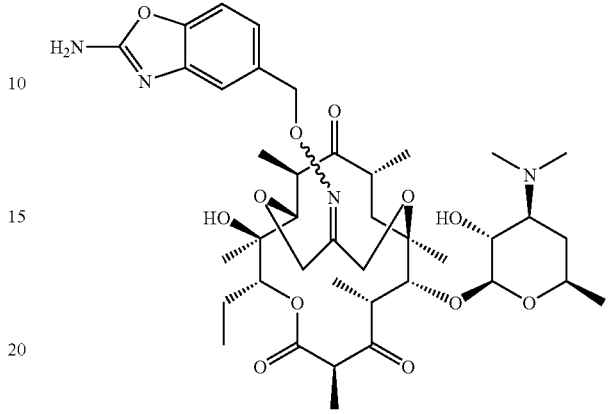

A solution of compound of step 2c (764 mg, 0.92 mmol) in 15 ml of methanol was stirred at 60° C. for 6 hours. The solvent was removed and the residue was purified on silica gel (2M NH$_3$ in MeOH/CH$_2$Cl$_2$=5/95) to give the title compound as a mixture of E/Z oxime isomers (690 mg, 95%, E/Z ~1/1). The compound was further separated on HPLC to give E-oxime isomer (280 mg) and Z-oxime isomer (230 mg).

E-oxime isomer: ESI MS m/e: 789 (M+H)$^+$.

E-oxime isomer: $^{13}$C NMR (125 MHz, CDCl$_3$): δ 218.5, 205.6, 191.7, 168.0, 162.0, 152.8, 148.6, 143.0, 134.0, 122.1, 117.0, 108.7, 103.3, 79.3, 79.0, 76.5, 75.8, 74.5, 70.5, 69.8, 66.1, 63.0, 61.5, 51.0, 47.0, 46.2, 40.5, 39.5, 39.3, 28.5, 23.5, 21.4, 20.0, 18.6, 18.0, 14.6, 14.2, 12.6, 12.2.

Z-oxime isomer: ESI MS m/e: 789 (M+H)$^+$.

Z-oxime isomer: $^3$C NMR (125 MHz, CDCl$_3$): δ 215.0, 205.7, 169.6, 162.2, 156.2, 149.0, 142.8, 131.4, 124.8, 116.3, 109.7, 102.5, 79.9, 78.7, 76.3, 76.2, 70.5, 69.7, 66.1, 59.2, 50.8, 46.3, 45.7, 40.5, 40.0, 39.1, 28.5, 23.1, 21.6, 19.7, 18.5, 17.2, 14.5, 13.1, 12.9, 11.8.

Example 3

In accordance with Schemes 1 and 2, the following compounds of the invention having the Formula II were prepared:

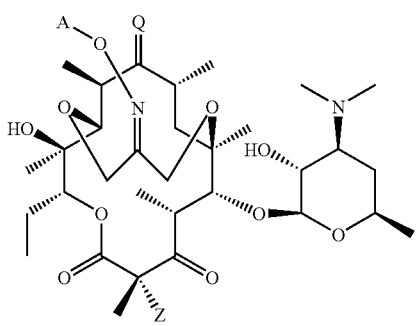

II wherein A, Q and Z are defined as in Table I.

TABLE I

| Example | A- | Q | Z | MS (ESI): m/z (M + H)+ | 13C NMR (125 MHz,CDCl3):δ |
|---|---|---|---|---|---|
| Example 01 | benzothiazol-6-ylmethyl | NAc | H | 831 | 205.8, 184.7, 178.0, 167.8, 154.3, 153.8, 153.0, 136.0, 134.0, 126.7, 123.5, 121.5, 103.1, 79.3, 79.2, 76.8, 75.8, 75.5, 74.7, 70.5, 69.7, 66.1, 63.1, 62.9, 50.7, 46.2, 40.5, 38.8, 37.2, 31.2, 28.5, 25.3, 23.8, 21.5, 20.3, 19.5, 17.8, 15.1, 14.1 |
| Example 02 | 2-amino-benzothiazol-6-ylmethyl | NAc | F | 864 | |
| Example 03 | benzo[1,2,5]thiadiazol-5-ylmethyl | NAc | H | 832 | |
| Example 04 | 2-amino-benzothiazol-5-ylmethyl | NAc | H | 846 | |
| Example 05 | benzoxazol-6-ylmethyl | NAc | H | 815 | 205.8, 184.7, 178.0, 167.8, 153.6, 153.0, 149.8, 140.3, 135.0, 126.3, 120.5, 110.8, 103.0, 79.4, 76.8, 76.0, 74.6, 70.5, 69.7, 66.1, 63.1, 62.8, 53.7, 50.7, 46.2, 40.5, 38.9, 28.5, 25.3, 23.8, 21.5, 20.3, 19.5, 17.8, 15.1, 14.1, 13.6, 12.9 |
| Example 06 | 3-amino-benzo[d]isoxazol-5-ylmethyl | NAc | H | 830 | |
| Example 07 | 3-amino-benzo[d]isoxazol-6-ylmethyl | NAc | H | 830 | |
| Example 08 | 2-amino-benzoxazol-6-ylmethyl | NAc | F | 848 | (selected)205.5, 205.3, 184.2, 165.1, 164.9, 162.4, 153.7, 148.8, 142.7, 131.2, 124.5, 116.2, 109.3, 104.1, 99.7, 98.1, 79.7, 76.5, 73.7, 70.6, 69.8, 66.0, 63.1, 62.6, 41.2, 40.5, 39.0, 28.4, 25.3, 24.7, 24.5, 23.2, 21.4, 21.0, 17.5, 15.0, 14.3, 12.6 |
| Example 09 | 2-amino-benzothiazol-6-ylmethyl | O | H | 805 | 218.4, 205.6, 168.0, 166.3, 152.0, 132.1, 131.9, 126.9, 121.5, 119.1, 103.3, 79.3, 78.9, 76.4, 75.9, 74.6, 70.5, 69.8, 66.1, 13.0, 61.5, 50.9, 47.1, 46.2, 40.5, 39.5, 39.3, 28.5, 23.5, 21.5, 20.1, 18.6, 18.0, 14.6, 14.2, 12.6, 12.2. |

TABLE I-continued

| Example | A- | Q | Z | MS (ESI): m/z (M + H)+ | 13C NMR (125 MHz, CDCl3):δ |
|---|---|---|---|---|---|
| Example 10 | H2N-benzoxazole-CH2- | NAc | H | 830 | 205.9, 184.7, 178.0, 167.9, 162.2, 153.4, 148.9, 142.6, 131.5, 124.6, 116.2, 109.4, 103.1, 79.3, 76.8, 74.8, 70.5, 66.1, 63.2, 62.9, 50.8, 40.5, 38.8, 28.5, 25.4, 23.8, 21.5, 20.3, 19.6, 17.8, 15.1, 14.1, 12.8. |
| Example 11 | H2N-benzoxazole-CH2- | O | H | 789 | 216.3, 203.6, 165.9, 160.1, 150.8, 146.8, 140.6, 129.1, 122.7, 114.1, 107.5, 101.2, 77.2, 76.8, 74.7, 74.4, 73.8, 72.6, 68.4, 67.7, 63.9, 60.8, 59.4, 51.5, 48.9, 45.0, 44.0, 38.3, 37.4, 29.0, 26.3, 21.3, 19.3, 18.0, 16.4, 15.9, 12.6, 12.1 |
| Example 12 | H2N-C(O)-NH-benzothiazole-CH2- | NAc | H | 889 | (selected): 205.8, 185.0, 178.3, 168.2, 161.6, 155.9, 153.4, 148.9, 133.0, 131.6, 126.6, 121.2, 120.0, 103.0, 79.4, 76.7, 76.2, 70.5, 69.7, 66.0, 63.2, 50.8, 46.2, 40.5, 38.8, 28.5, 25.5, 23.7, 21.5, 20.2, 19.7, 18.0, 15.4, 14.1, 13.7, 12.7. |
| Example 13 | H2N-(4-F-benzothiazole)-CH2- | NAc | H | 864 | (selected): 205.9, 184.7, 178.0, 167.9, 167.4, 153.9, 153.7, 152.0, 140.1, 140.0, 133.7, 132.9, 132.8, 116.4, 112.4, 112.3, 103.0, 79.3, 76.7, 75.6, 74.8, 70.5, 59.7, 66.0, 63.1, 62.9, 50.8, 46.3, 40.4, 38.8, 28.5, 25.3, 23.7, 21.5, 20.3, 19.6, 17.8, 15.1, 14.1, 13.7, 12.8 |
| Example 14 | H2N-C(O)-NH-benzothiazole-CH2- | O | H | 848 | (selected); 217.9, 205.6, 168.9, 162.0, 155.5, 152.9, 131.8, 126.8, 122.1, 119.7, 102.8, 9.4, 79.3, 76.5, 75.1, 70.5, 69.8, 66.1, 63.2, 50.9, 46.6, 46.3, 40.5, 39.4, 28.5, 23.2, 21.5, 18.2, 17.9, 14.2, 14.0, 13.2, 12.2. |
| Example 15 | H2N-(4-F-benzothiazole)-CH2- | O | H | 823 | (selected): 218.4, 205.7, 168.1, 167.4, 154.0, 153.1, 152.0, 140.2, 140.0, 133.8, 133.7, 132.8, 132.7, 116.7, 112.7, 112.5, 103.3, 79.3, 78.9, 76.8, 75.9, 75.8, 74.7, 70.5, 69.8, 66.0, 62.9, 61.5, 51.0, 47.2, 46.2, 40.4, 39.4, 39.3, 28.5, 23.5, 21.5, 20.1, 18.5, 18.0, 14.7, 14.2, 12.5, 12.2 |
| Example 16 | H2N-indazole-CH2- | NAc | H | 829 | |
| Example 17 | H2N-benzoxazole-CH2- | NAc | H | 830 | 205.9, 191.4, 186.8, 184.7, 178.1, 167.8, 162.1, 153.3, 148.5, 143.0, 134.1, 125.6, 121.9, 116.8, 108.7, 103.0, 79.4, 76.4, 74.6, 70.5, 69.8, 66.1, 63.2, 62.9, 50.8, 40.5, 38.8, 31.2, 28.5, 25.3, 23.8, 21.5, 19.5, 17.8, 15.1, 14.1, 12.8. |
| Example 18 | H2N-benzoxazole-CH2- | O | H | 789 | 218.5, 205.6, 191.7, 168.0, 162.0, 152.8, 148.6, 143.0, 134.0, 122.1, 117.0, 108.7, 103.3, 79.3, 79.0, 76.5, 75.8, 74.5, 70.5, 69.8, 66.1, 63.0, 61.5, 51.0, 47.0, 46.2, 40.5, 39.5, 39.3, 28.5, 23.5, 21.4, 20.0, 18.6, 18.0, 14.6, 14.2, 12.6, 12.2. |

TABLE I-continued

| Example | A- | Q | Z | MS (ESI): m/z (M + H)+ | 13C NMR (125 MHz,CDCl3):δ |
|---|---|---|---|---|---|
| Example 19 | *acetamido-benzothiazol-6-ylmethyl* | NAc | H | 888 | |
| Example 20 | *3-amino-1H-pyrazolo[3,4-b]pyridin-5-ylmethyl* | NAc | H | 830 | |
| Example 21 | *3-amino-benzo[d]isoxazol-5-ylmethyl* | NAc | F | 848 | |
| Example 22 | *3-amino-1H-indazol-5-ylmethyl* | NAc | F | 847 | |
| Example 23 | *2-amino-1H-benzimidazol-6-ylmethyl* | NAc | H | 829 | (selected); 206.2, 184.8, 168.6, 155.0, 153.8, 110.0, 103.4, 79.5, 76.7, 75.1, 70.5, 69.8, 66.0, 63.2, 63.0, 51.3, 40.5, 38.8, 31.2, 30.0, 28.4, 25.4, 23.7, 21.8, 20.6, 20.0, 17.9, 15.1, 14.1, 12.8. |
| Example 24 | *2-amino-1H-benzimidazol-6-ylmethyl* | O | H | 788 | (selected): 218.5, 206.0, 168.8, 155.1, 153.3, 129.8, 121.1, 103.4, 79.6, 79.1, 76.6, 75.4, 70.6, 69.8, 66.0, 62.9, 62.1, 53.7, 51.4, 47.6, 46.0, 40.5, 39.7, 39.4, 28.4, 23.4, 21.5, 20.4, 18.6, 18.2, 15.3, 14.4, 12.5, 12.2. |
| Example 25 | *2-(thiazol-2-yl)-1H-benzimidazol-6-ylmethyl* | NAc | H | 897 | 205.8, 184.8, 178.0, 167.9, 167.8, 159.3, 153.5, 153.3, 146.3, 143.8, 143.7, 135.0, 133.9, 1333.3, 125.4, 123.7, 121.9, 120.2, 111.1, 103.0, 79.4, 79.2, 76.5, 76.4, 74.8, 70.5, 69.8, 66.1, 63.2, 62.9, 50.8, 46.2, 40.5, 38.8, 28.5, 25.4, 23.8, 21.5, 20.3, 19.6, 17.8, 15.1, 14.1, 13.7, 12.9. |
| Example 26 | *benzoxazol-5-ylmethyl* | NAc | H | 815 | 205.8, 184.7, 178.0, 167.8, 153.6, 153.0, 149.8, 140.3, 135.0, 126.3, 120.5, 110.8, 103.0, 78.4, 76.0, 74.6, 70.5, 69.7, 66.2, 63.1, 62.9, 50.7, 46.2, 40.5, 38.8, 28.6, 25.4, 23.8, 21.5, 20.3, 19.5, 17.8, 15.1, 14.1, 13.6, 12.9 |
| Example 27 | *benzoxazol-5-ylmethyl* | O | H | 775 | 218.4, 205.6, 168.0, 153.0, 149.8, 140.3, 134.9, 126.5, 120.7, 110.8, 103.1, 79.3, 79.0, 76.1, 75.8, 74.6, 70.5, 69.6, 66,2, 63.0, 61.5, 50.9, 47.0, 46.2, 40.5, 39.5, 39.3, 28.9, 23.5, 21.4, 20.0, 18.6, 18.0, 14.6, 14.3, 12.6, 12.2 |

TABLE I-continued

| Example | A- | Q | Z | MS (ESI): m/z (M + H)+ | 13C NMR (125 MHz,CDCl3):δ |
|---|---|---|---|---|---|
| Example 28 | thiazole-oxazole-benzo | NAc | H | 898 | 205.8, 184.7, 178.0, 167.8, 157.5, 155.1, 153.7, 150.5, 145.3, 141.6, 135.9, 127.1, 123.3, 120.4, 111.1, 103.0, 79.4, 76.8, 75.8, 74.6, 70.5, 69.7, 66.1, 63.1, 62.9, 50.7, 40.5, 38.8, 29.9, 29.5, 28.5, 25.4, 23.8, 21.5, 20.3, 19.5, 17.8, 15.1, 14.1, 13.6, 12.9. |
| Example 29 | pyrazole-oxazole-benzo | NAc | H | 881 | |
| Example 30 | methoxy-oxazole-benzo | NAc | H | 845 | |
| Example 31 | allylamino-oxazole-benzo | NAc | H | 870 | (selected): 210.1, 184.7, 177.9, 170.0, 162.4, 153.7, 148.5, 143.1, 133.9, 132.9, 121.5, 119.6, 116.4, 108.7, 102.4, 81.2, 79.7, 76.6, 76.3, 74.5, 70.6, 69.5, 66.2, 62.7, 60.8, 43.7, 40.7, 40.5, 40.1, 39.3, 37.4, 29.0, 25.3, 22.7, 21.6, 21.4, 20.6, 19.8, 18.3, 16.2, 14.8, 12.5 |
| Example 32 | hydroxy-amino-pyridine | NAc | H | 806 | (selected): 206.1, 184.9, 178.0, 168.1, 153.8, 150.1, 120.4, 113.7, 103.0, 79.4, 76.7, 70.5, 69.7, 66.0, 50.9, 40.5, 28.7, 25.4, 23.7, 21.5, 17.8, 17.2, 15.7, 15.1, 14.1, 12.8, 12.0. |
| Example 33 | oxazolo-pyridine | NAc | H | 816 | |
| Example 34 | amino-oxazolo-pyridine | NAc | H | 831 | (selected): 205.9, 184.8, 177.9, 167.9, 165.1, 157.6, 153.8, 152.9, 140.5, 115.5, 114.9, 102.9, 79.3, 76.8, 76.7, 75.1, 70.5, 69.6, 66.1, 63.1, 50.9, 40.5, 38.8, 28.7, 25.6, 25.4, 23.8, 21.6, 21.5, 20.4, 19.6, 17.8, 17.2, 15.2, 14.1, 12.8, 12.0. |
| Example 35 | diallylamino-oxazole-benzo | NAc | H | 910 | (selected): 209.9, 184.7, 177.8, 169.9, 157.6, 153.9, 144.3, 133.6, 133.3, 132.8, 131.0, 121.1, 119.7, 118.1, 108.5, 107.6, 102.4, 81.0, 79.7, 76.5, 76.0, 74.4, 70.5, 69.5, 66.3, 62.7, 62.6, 60.7, 45.1, 43.7, 40.6, 39.3, 29.2, 25.3, 22.9, 21.5, 20.6, 19.8, 18.2, 16.3, 14.7, 12.7. |
| Example 36 | benzotriazole | NAc | H | 815 | |

TABLE I-continued

| Example | A- | Q | Z | MS (ESI): m/z (M + H)+ | 13C NMR (125 MHz,CDCl3):δ |
|---|---|---|---|---|---|
| Example 37 | (1-methyl-benzotriazol-5-yl)methyl | NAc | H | 829 | |
| Example 38 | (2-amino-benzoxazol-5-yl)methyl | NC(O)OCH3 | H | 846 | 205.9, 186.4, 167.7, 163.7, 162.4, 153.2, 148.4, 143.0, 134.1, 121.8, 116.6, 108.7, 102.9, 79.5, 78.9, 77.5, 76.8, 76.4, 75.1, 74.7, 70.5, 69.7, 66.1, 63.2, 62.7, 54.1, 53.1, 50.7, 40.5, 38.7, 32.0, 29.5, 28.6, 23.8, 21.5, 20.2, 19.3, 17.8, 14.9, 14.1, 12.9, |
| Example 39 | (2-amino-benzoxazol-5-yl)methyl | NH | H | 788 | 205.2, 169.3, 162.8, 153.7, 148.5, 143.1, 133.7, 121.6, 116.5, 108.8, 103.5, 80.4, 78.8, 78.6, 76.6, 75.9, 70.6, 69.8, 66.1, 64.7, 63.1, 51.6, 47.9, 41.4, 40.5, 38.3, 28.5, 23.0, 21.4, 21.1, 20.1, 17.4, 15.8, 14.4, 14.0, 11.8 |

In accordance with Scheme 1, compounds of the invention having the Formula IX were prepared:

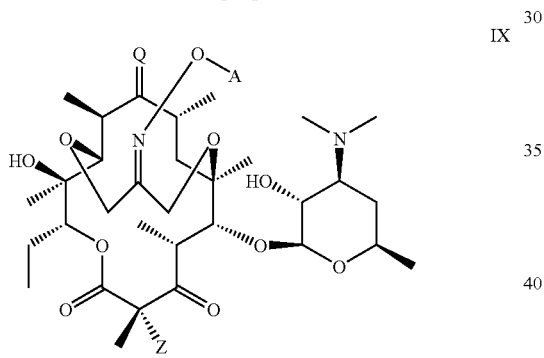

IX wherein A, Q, and Z are defined as in Table II.

TABLE II

| Example | A- | Q | Z | MS (ESI): m/z (M + H)+ | 13C NMR (125 MHz,CDCl3):δ |
|---|---|---|---|---|---|
| Example 01 | benzoxazol-6-ylmethyl | NAc | H | 815 | 205.8, 184.6, 176.5, 169.3, 156.2, 153.0, 149.9, 140.3, 134.8, 126.6, 120.8, 110.9, 102.6, 79.6, 79.0, 76.3, 76.2, 70.5, 69.7, 66.1, 58.4, 50.9, 45.4, 40.5, 29.9, 28.6, 25.5, 23.4, 21.6, 20.2, 19.7, 17.2, 15.6, 14.4, 12.9, 12.0 |
| Example 02 | (2-amino-benzothiazol-6-yl)methyl | O | H | 805 | 215.1, 205.7, 169.6, 166.8, 156.2, 152.1, 132.0, 126.6, 121.3, 118.9, 102.5, 80.0, 78.7, 76.3, 76.1, 70.5, 69.7, 66.0, 50.8, 46.3, 45.7, 40.4, 40.0, 39.1, 28.5, 23.1, 21.6, 19.7, 18.5, 17.3, 14.5, 13.1, 11.8 |

TABLE II-continued

| Example | A- | Q | Z | MS (ESI): m/z (M + H)+ | 13C NMR (125 MHz,CDCl3):δ |
|---|---|---|---|---|---|
| Example 03 | benzoxazol-2-amine-6-ylmethyl | O | H | 789 | 215.0, 205.7, 169.6, 162.2, 156.2, 149.0, 142.8, 131.4, 124.8, 116.3, 109.7, 102.5, 79.9, 78.7, 76.3, 76.2, 70.5, 69.7, 66.1, 59.2, 50.8, 46.3, 45.7, 40.5, 40.0, 39.1, 28.5, 23.1, 21.6, 19.7, 18.5, 17.2, 14.5, 13.1, 12.9, 11.8. |
| Example 04 | 4-fluorobenzothiazol-2-amine-6-ylmethyl | NAc | H | 864 | (selected): 205.9, 184.6, 176.4, 169.4, 166.7, 156.4, 154.2, 152.2, 140.1, 140.0, 134.0, 133.9, 133.3, 133.2, 116.6, 116.5, 112.6, 112.4, 102.6, 79.6, 79.0, 76.2, 75.8, 75.4, 70.5, 69.7, 66.1, 58.5, 50.9, 45.4, 40.5, 39.0, 28.5, 25.5, 23.3, 21.6, 20.2, 19.7, 17.2, 15.7, 14.4, 13.0, 12.0. |
| Example 05 | 2-ureidobenzothiazol-6-ylmethyl | O | H | 848 | (selected): 216.3, 205.4, 169.6, 162.0, 155.8, 149.0, 131.9, 127.1, 119.6, 102.3, 80.0, 79.0, 76.7, 76.3, 76.0, 70.5, 69.7, 66.0, 59.4, 50.7, 46.3, 45.7, 40.5, 40.1, 39.3, 29.9, 28.6, 23.1, 21.6, 19.8, 18.2, 17.4, 14.5, 13.7, 13.0, 11.7. |
| Example 06 | 4-fluorobenzothiazol-2-amine-6-ylmethyl | O | H | 823 | (selected): 215.2, 205.7, 169.6, 167.2, 156.5, 154.1, 152.1, 140.2, 140.1, 134.0, 133.9, 133.0, 132.9, 116.6, 112.5, 112.3, 102.5, 76.3, 70.5, 69.7, 66.1, 59.1, 50.9, 46.3, 45.7, 40.5, 39.2, 28.5, 23.1, 21.6, 19.7, 18.5, 17.2, 14.5, 13.2, 12.8, 11.8 |
| Example 07 | benzoxazol-2-amine-5-ylmethyl | NAc | H | 830 | |

In accordance with Scheme I, compounds of the invention having the Formula X were prepared:

Formula X (macrolide structure with substituents A–O, X, Z)

wherein A, X and Z are defined as in Table III.

TABLE III

| Example | A- | X | Z | MS (ESI): m/z (M + H)+ |
|---|---|---|---|---|
| Example 01 | benzoxazol-2-amine-5-ylmethyl | NH2 | H | 790 |

Example 4

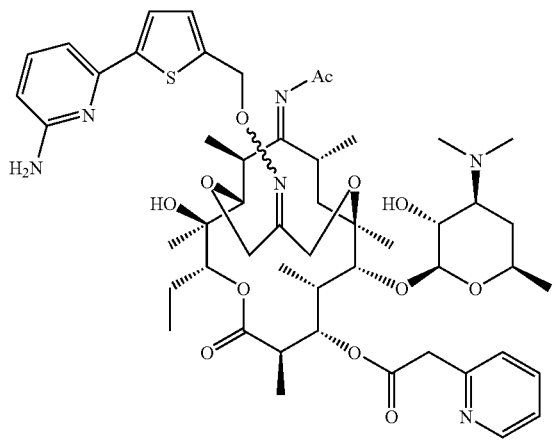

Step 4a:

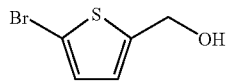

A solution of 5-bromo-2-thiophenecarboxaldehyde (13.08 g, 68.46 mmol) in isopropanol (100 mL) was treated with NaBH$_4$ (1.30 g, 34.23 mmol) at 0° C. for 1.5 hours with stirring before HCl (1 M, 60 mL, 60 mmol) was charged. The mixture was stirred for 0.5 hour before being partitioned (ethyl acetate and saturated NaHCO$_3$). The organics were washed with water, brine, and then dried (Na$_2$SO$_4$). The volatile was removed by evaporation and dried in a vacuum to give the title compound (12.55 g, 95%).

Step 4b:

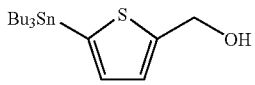

Into a solution of the compound of Step 4a (5.02 g, 26.00 mmol) in THF (80 mL) was treated with NaH (95%, 730 mg, 28.9 mmol) at room temperature for 50 minutes with stirring. It was chilled to −78° C. before n-BuLi (1.6 M in hexanes, 20 mL, 32 mmol) was charged. The mixture was kept at −78° C. for 1 hour before n-Bu$_3$SnCl (17.6 mL, 65 mmol) was introduced. The mixture was warmed up naturally to room temperature and stirred over night. The volatile was evaporated off and the residue was partitioned (ethyl acetate and saturated NaHCO$_3$). The organics were washed with water, brine, and then dried (Na$_2$SO$_4$). Evaporation followed by chromatography (silica, hexanes/ethyl acetate) gave the title compound (4.51 g, 43%).

Step 4c:

Into a 250 mL round bottom flask was charged 2-amino-6-bromopyridine (25.0 g, 0.144 mol) and phthalic anhydride (21.4 g, 0.144 mol). The solid mixture in the open flask (with a slow flow of N$_2$) was heated to 175° C. and the temperature was kept there for 1 hour or until no vapor comes out. It was cooled down to room temperature and vacuumed for 10 hours to give the title compound as a tan solid (100% yield).

Step 4d:

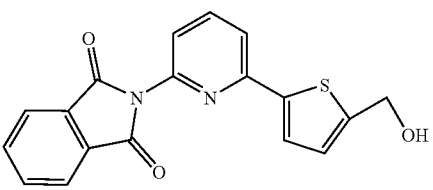

A mixture of the compound from Step 4b (4.50 g, 11.16 mmol), the compound from Step 4c (3.72 g, 12.28 mmol), and Pd(PPh$_3$)$_4$ (645 mg, 0.56 mmol) in PhMe (50 mL) was degassed and heated at 100° C. under N$_2$ for 17 hours before being cooled to 0° C. The insoluble was collected by filtration and washed with PhMe to give the title compound (2.90 g). The filtrate and washings were evaporated and the residue was chromatographed (silica, hexanes/ethyl acetate) to give another crop of the title compound (0.20 g).

ESIMS m/e: 337 (M+H)$^+$.

Step 4e:

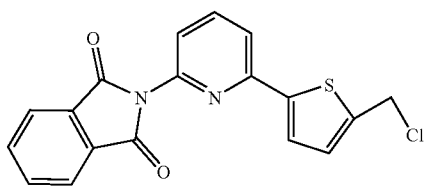

A suspension of the compound from Step 4d (3.10 g, 9.22 mmol) in methylene chloride (50 mL) was treated with thionyl chloride (3.35 mL, 46.08 mmol) at 0° C. The mixture was warmed up naturally to room temperature and stirred for 16 hours. The volatile was evaporated off. The residue was partitioned (CH$_2$Cl$_2$/saturated NaHCO$_3$). The organics were washed with water, brine, and then dried (Na$_2$SO$_4$). The volatile was removed by evaporation and dried in vacuo to give the title compound (3.253 g, 100%).

ESIMS m/e: 355/357 (M+H)$^+$.

Step 4f:

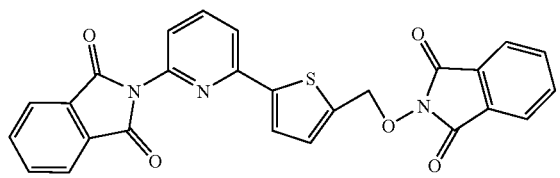

Into a solution of N-hydroxylphthalimide (2.40 g, 14.7 mmol) in DMF (20 mL) was added NaH (95%, 332 mg, 13.8 mmol) at 0° C. It was warmed up to room temperature and stirred for 1 hour. It was added into a solution of the compound from Step 4e (3.25 g, 9.2 mmol) in DMF (25 mL). The mixture was stirred at 40° C. for 16 hours before being cooled to room temperature. It was diluted with saturated NaHCO$_3$ and water. The insoluble was collected by filtration, washed with saturated NaHCO$_3$ and water, and dried to give the title compound (3.930 g, 89%).
ESIMS m/e: 482 (M+H)$^+$.

Step 4g:

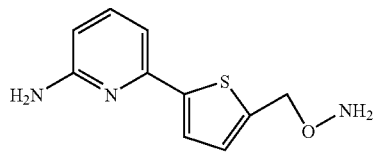

A suspension of the compound from Step 4f (1.00 g, 2.08 mmol) in methanolic ammonia (2M, 20 mL, 40 mmol) was heated at 55° C. for 2 hours before being cooled to room temperature. The insoluble was filtered off and washed with MeOH. The combined filtrate and washings were evaporated. The residue was added CH$_2$Cl$_2$ to dissolve the crude title compound (548 mg) after evaporation.
ESIMS m/e: 222 (M+H)$^+$.

Step 4h:

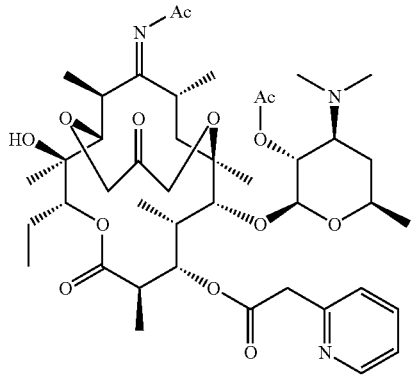

A mixture of compound of formula VIII where X and Y taken together with the atom that they are attached is C=N—Ac, U=H, V=OH, Z=H, Rp=Ac and W=NMe$_2$ (356 mg, 0.50 mmol), 2-pyridylacetic acid hydrochloride (174 mg, 1.0 mmol), 1-(3-dimethylaminopropyl)-3-ethylcarbodiimide hydrochloride (EDC.HCl, 192 mg, 1.0 mmol), triethylamine (0.28 mL, 2.0 mmol) and DMAP (10.0 mg) in methylene chloride (5.0 mL) was stirred at room temperature for 22 hours before more 2-pyridylacetic acid hydrochloride (87 mg, 0.5 mmol) and EDC.HCl (192 mg, 1.0 mmol). It was stirred for another 3 hours before being partitioned (ethyl acetate and 10% K$_2$CO$_3$). The organics were washed with water, brine, and then dried (Na$_2$SO$_4$). The volatile was removed by evaporation and dried in a vacuum to give a yellow foam (450 mg) as the crude title compound.
ESIMS m/e: 832 (M+H)$^+$.

Step 4i:

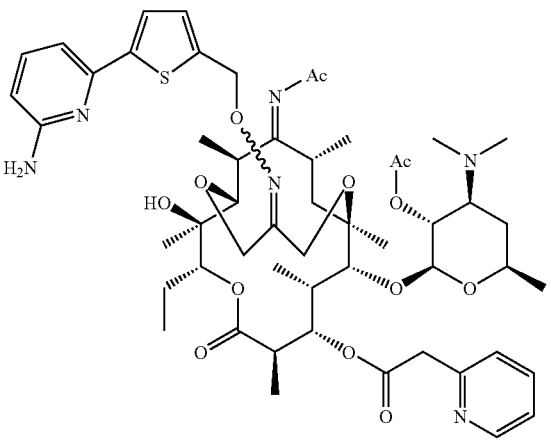

Into a solution of the crude compound from Step 4g (166 mg, ~0.62 mmol) in ethanol (5.0 mL) and HCl (1 M, 2.5 mL) at −5° C. was added the crude compound from Step 4h (450 mg, 0.5 mmol at most). After being stirred for one hour, more crude compound from Step 4g (50 mg, ~0.18 mmol) was added. The mixture was stirred for another 1 hour before partition (ethyl acetate and saturated NaHCO$_3$). The organics were washed with water, brine, and then dried (Na$_2$SO$_4$). It was evaporated and the residue was chromatographed (silica, hexanes/acetone) to give the title compound (332 mg, 64%) as a 2:1 mixture.
ESIMS m/e: 1035 (M+H)$^+$.

Step 4j:

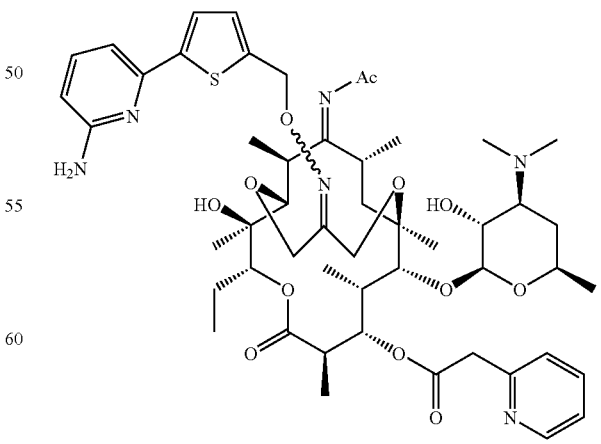

A solution of the compound from Step 4i (100 mg) in MeOH (3 mL) was stirred at room temperature for 70 hours before evaporation to give the title compound. The two bridged oxime isomers were separated by HPLC.

E-oxime isomer: ESIMS m/e: 993 (M+H)+. $^{13}$C NMR (CDCl$_3$, 125 MHz): 184.6, 178.0, 172.5, 170.4, 158.0, 153.9, 153.2, 151.0, 149.1, 145.4, 141.8, 138.1, 136.6, 127.5, 124.4, 123.7, 122.3, 109.1, 106.7, 103.0, 82.3, 79.4, 78.5, 78.3, 76.4, 75.0, 70.8, 70.5, 69.1, 65.4, 63.1, 62.4, 43.8, 42.7, 40.4, 39.9, 38.3, 36.8, 35.8, 29.7, 29.2, 25.1, 23.2, 21.0, 19.9, 19.1, 17.5, 15.0, 14.3, 12.1, 9.0.

Z-oxime isomer: ESIMS m/e: 993 (M+H)+. $^{13}$C NMR (CDCl$_3$, 125 MHz): 184.4, 176.6, 173.7, 170.2, 158.0, 156.1, 153.9, 151.1, 149.1, 145.5, 141.2, 138.1, 136.6, 128.0, 124.4, 123.8, 122.3, 109.1, 106.7, 103.0, 83.3, 80.2, 79.0, 77.7, 77.5, 75.8, 70.8, 70.6, 70.5, 69.1, 65.4, 58.7, 43.2, 40.3, 39.1, 38.5, 36.5, 36.0, 29.7, 29.2, 25.2, 22.7, 21.1, 20.1, 19.6, 16.8, 15.4, 14.6, 11.3, 9.1.

Example 5

Compounds with Improved Antibacterial Activities

Table IV below provides MIC data of species from U.S. Pat. No. 6,878,691 and U.S. Patent Application Publication No. 2004/0053861.

The values in the table are minimum inhibition concentration (MIC) and are expressed as ug/mL.

Assays for MIC are described above.

TABLE IV

| Compound | Structure | S. aureus 29213 | S. aureus 27660 | S. aureus 33591 | S. pneumoniae 7701 | S. pneumoniae 700906 | S. pyogenes 1323 | S. pyogenes 2912 | H. influenzae 33929 |
|---|---|---|---|---|---|---|---|---|---|
| A1 | 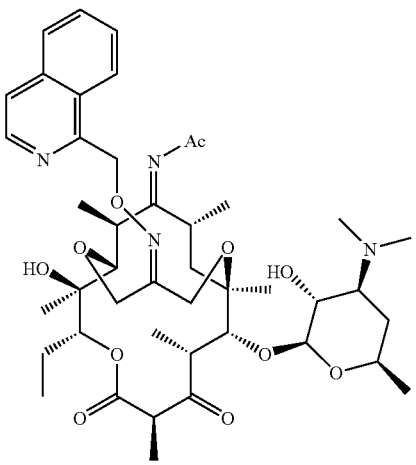 | 0.25 | 0.13 | >64 | 0.5 | 0.25 | 0.5 | 8 | 8 |
| A2 | 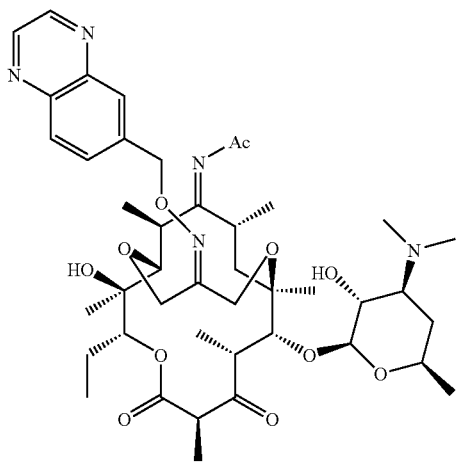 | 0.5 | 0.25 | >64 | 0.5 | 0.25 | 1 | 16 | 16 |

TABLE IV-continued

| Compound | Structure | S. aureus 29213 | S. aureus 27660 | S. aureus 33591 | S. pneumoniae 7701 | S. pneumoniae 700906 | S. pyogenes 1323 | S. pyogenes 2912 | H. influenzae 33929 |
|---|---|---|---|---|---|---|---|---|---|
| A3 | 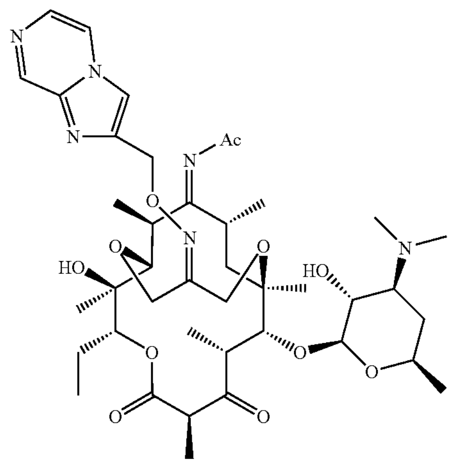 | 0.25 | 0.25 | >64 | 2 | 0.13 | 16 | 32 | 8 |
| A4 | 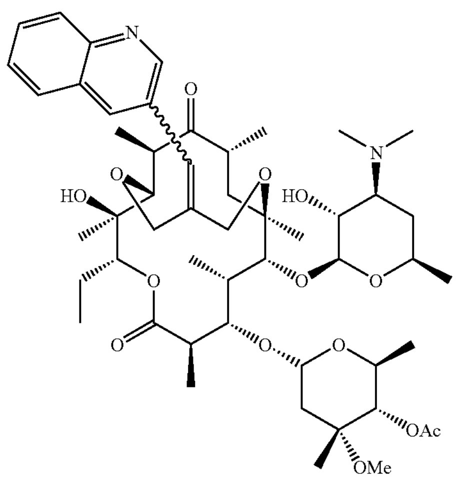 | | | | | 8 | 64 | 64 | >64 |
| A5 | 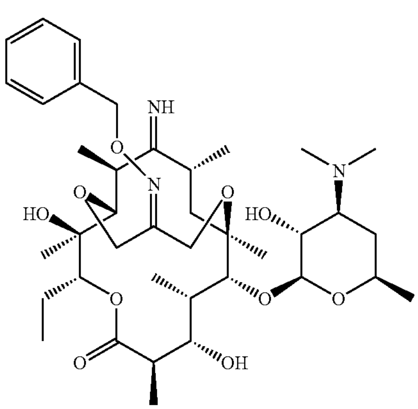 | | | | >64 | 2 | 64 | >64 | >64 |

TABLE IV-continued

| Compound | Structure | S. aureus 29213 | S. aureus 27660 | S. aureus 33591 | S. pneumoniae 7701 | S. pneumoniae 700906 | S. pyogenes 1323 | S. pyogenes 2912 | H. influenzae 33929 |
|---|---|---|---|---|---|---|---|---|---|
| A6 | 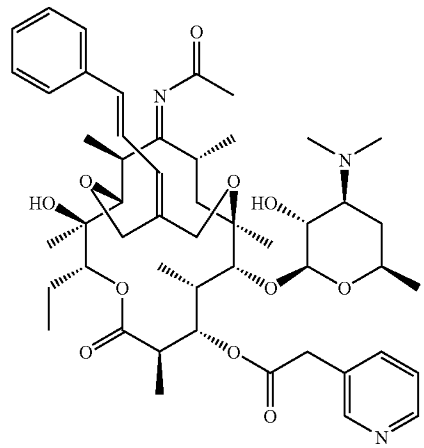 | 1 | 1 | 16 | 1 | 8 | 2 | 8 | >64 |

Table V provides data for compounds of this invention demonstrating improved microbiological activities against gram negative bacteria and resistant organism. The values in Table V are minimum inhibition concentration and are expressed as ug/mL.

TABLE V

| Compound | Structure | S. aureus 29213 | S. aureus 27660 | S. aureus 33591 | S. pneumoniae 7701 | S. pneumoniae 700906 | S. pyogenes 1323 | S. pyogenes 2912 | H. influenzae 33929 |
|---|---|---|---|---|---|---|---|---|---|
| B1 | 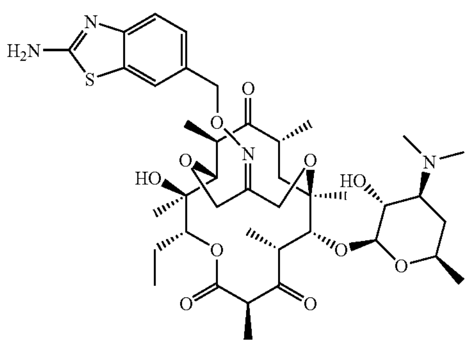 | <=0.06 | <=0.06 | >64 | <=0.06 | 1 | 0.25 | 4 | 2 |
| B2 | 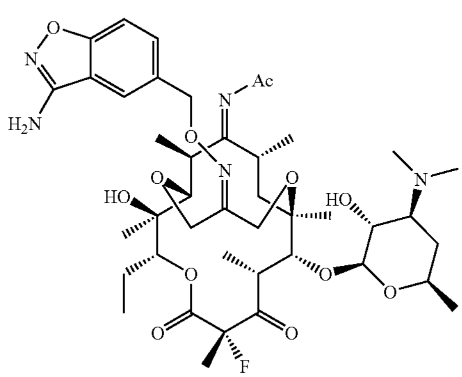 | 0.125 | <=0.06 | >64 | 0.125 | 0.5 | 0.5 | 2 | 2 |

TABLE V-continued

| Compound | Structure | S. aureus 29213 | S. aureus 27660 | S. aureus 33591 | S. pneumoniae 7701 | S. pneumoniae 700906 | S. pyogenes 1323 | S. pyogenes 2912 | H. influenzae 33929 |
|---|---|---|---|---|---|---|---|---|---|
| B3 | 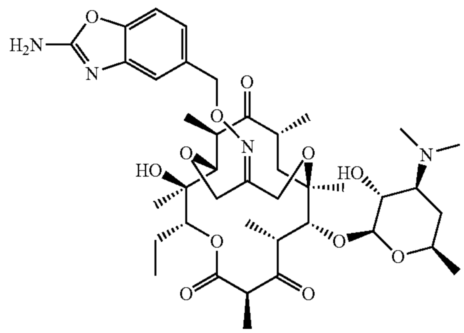 | <=0.06 | <=0.06 | 32 | 0.125 | 0.25 | 0.5 | 4 | 2 |
| B4 | 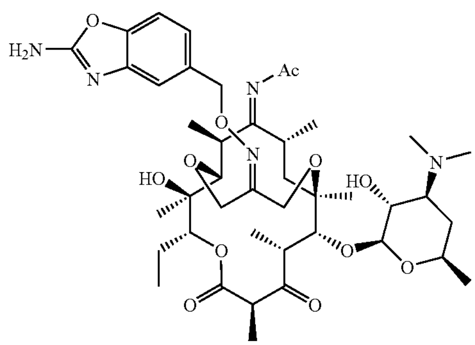 | 0.125 | 0.125 | 32 | 0.125 | 0.125 | 0.5 | 1 | 4 |

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound of formula II

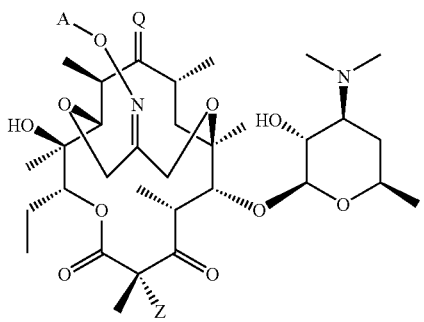

wherein A is:

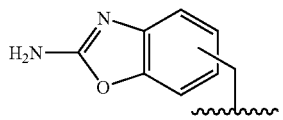

or their racemates, enantiomers, regioisomers, salts, esters or prodrugs thereof, wherein Z is hydrogen or halogen and Q is O, $NR_1$, or $NC(O)R_1$, where $R_1$ is independently selected from the group consisting of hydrogen, acyl, silane, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group.

2. A compound of claim 1 wherein A is:

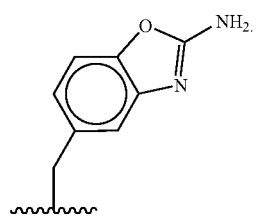

3. A compound having the Formula II:

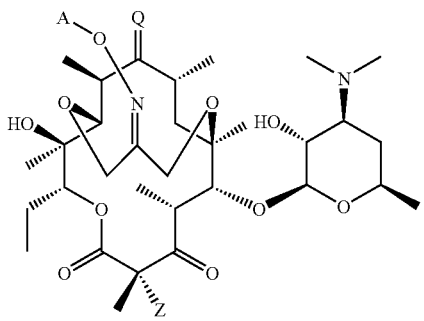

wherein A, Q, and Z are as defined in Table C:

TABLE C

| Number | A | Q | Z |
|---|---|---|---|
| 08 | H₂N-benzoxazole-CH₂- | NAc | F |
| 10 | H₂N-benzoxazole-CH₂- | NAc | H |
| 11 | H₂N-benzoxazole-CH₂- | O | H |
| 17 | H₂N-benzoxazole-CH₂- | NAc | H |
| 18 | H₂N-benzoxazole-CH₂- | O | H |
| 38 | H₂N-benzoxazole-CH₂- | NC(O)OCH₃ | H |
| 39 | H₂N-benzoxazole-CH₂- | NH | H |

4. A compound having the Formula IV:

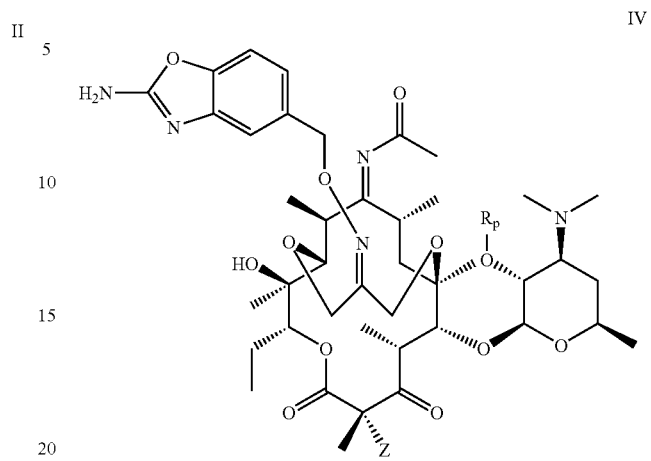

wherein $R_p$ is hydrogen, hydroxy protecting group or hydroxy prodrug group and Z is hydrogen or halogen.

5. A compound represented by Formula V:

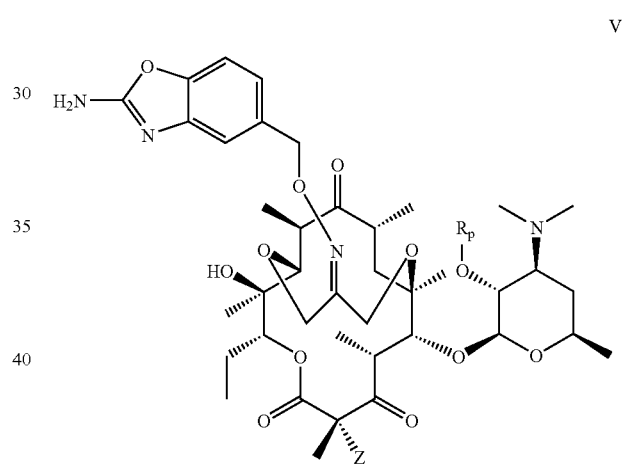

wherein $R_p$ is hydrogen, hydroxy protecting group or hydroxy prodrug group and Z it hydrogen or halogen.

6. A compound according to claim 4 where $R_p$ is hydrogen and Z is hydrogen.

7. A compound according to claim 5 where $R_p$ is hydrogen and Z is hydrogen.

8. A pharmaceutical composition comprising a compound of claim 1 or a pharmaceutically acceptable salt, ester or prodrug thereof, in combination with a pharmaceutically acceptable carrier.

9. A method of treating a bacterial infection in a subject in need of such treatment comprising, administering to said subject a pharmaceutical composition of claim 8.

10. A method of treating inflammation in a subject in need of such treatment comprising, administering to said subject a pharmaceutical composition of claim 8.

11. A method of treating cystic fibrosis in a subject in need of such treatment comprising, administering to said subject a pharmaceutical composition of claim 8.

* * * * *